(12) United States Patent
Nagai et al.

(10) Patent No.: US 10,732,181 B2
(45) Date of Patent: Aug. 4, 2020

(54) METHOD FOR DETECTING LIPID BILAYER MEMBRANE PARTICLES OR FRAGMENTS THEREOF

(71) Applicant: Nihon Kohden Corporation, Tokyo (JP)

(72) Inventors: Yutaka Nagai, Saitama (JP); Masashi Takao, Sendai (JP); Masami Ito, Saitama (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 16 days.

(21) Appl. No.: 15/952,749

(22) Filed: Apr. 13, 2018

(65) Prior Publication Data

US 2018/0299452 A1 Oct. 18, 2018

(30) Foreign Application Priority Data

Apr. 17, 2017 (JP) .................................. 2017-081568
Jun. 30, 2017 (JP) .................................. 2017-129524

(51) Int. Cl.
*G01N 33/553* (2006.01)
*G01N 33/574* (2006.01)
*G01N 21/64* (2006.01)
*G01N 33/68* (2006.01)

(52) U.S. Cl.
CPC ... *G01N 33/57488* (2013.01); *G01N 21/6428* (2013.01); *G01N 33/553* (2013.01); *G01N 33/6842* (2013.01); *G01N 33/6872* (2013.01); *G01N 2021/6439* (2013.01); *G01N 2333/70596* (2013.01)

(58) Field of Classification Search
CPC ........... G01N 33/57488; G01N 33/553; G01N 33/6842; G01N 33/6872; G01N 21/6428; G01N 2021/6439; G01N 2333/70596
See application file for complete search history.

(56) References Cited

U.S. PATENT DOCUMENTS

2012/0208293 A1 8/2012 Higashi et al.
2015/0301058 A1* 10/2015 Schettini ................ G01N 33/53
424/193.1
2017/0045451 A1* 2/2017 Nolan .................. G01N 33/542

FOREIGN PATENT DOCUMENTS

JP  2012168012 A   9/2012
JP   201315517 A   1/2013
JP  2014236685 A  12/2014
WO 2014082083 A1   5/2014

OTHER PUBLICATIONS

Yoshioka et al., "Exosome provides new insight into liquid biopsy," Cytometry Research (2016); 26(1):1-6, Abstract only.
Extended European Search Report dated Sep. 14, 2018 for EP Application No. 18167512.5.
Kanwar et al., "Microfluidic device (ExoChip) for on-chip isolation, quantification and characterization of circulating exosomes," Lab Chip (2014); 14:1891-1900.

* cited by examiner

*Primary Examiner* — Gailene Gabel
(74) *Attorney, Agent, or Firm* — Fox Rothschild LLP

(57) ABSTRACT

Disclosed is a method for detecting lipid bilayer membrane particles or fragments thereof, having predetermined molecules existing on surfaces thereof, in a biological sample collected from a subject, the method comprising: adding to the biological sample a dye that stains a lipid bilayer membrane; adding a substance that specifically binds to the predetermined molecules; trapping the substance bound to the predetermined membrane molecules and separating unbound components; and detecting the separated stained lipid bilayer membrane particles or fragments thereof by measurement of the dye emission spectrum. The specific binding substance is conjugated to a magnetic bead or binds to a magnetic bead, the trapping and separating steps are performed magnetically, and the particle size of the magnetic bead is equal to or less than the minimum detection sensitivity of the measurement system.

19 Claims, 24 Drawing Sheets

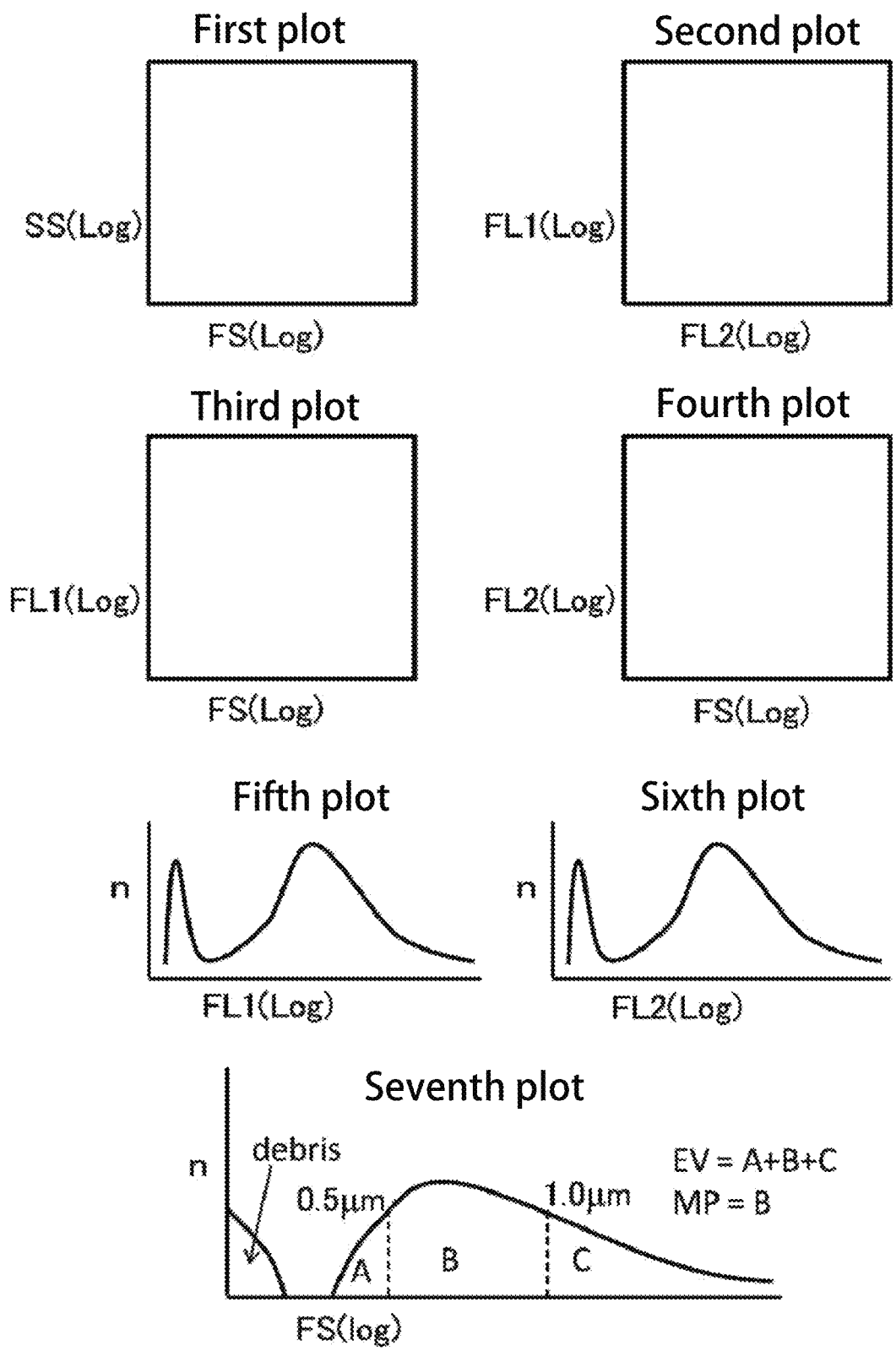

FIG. 9A
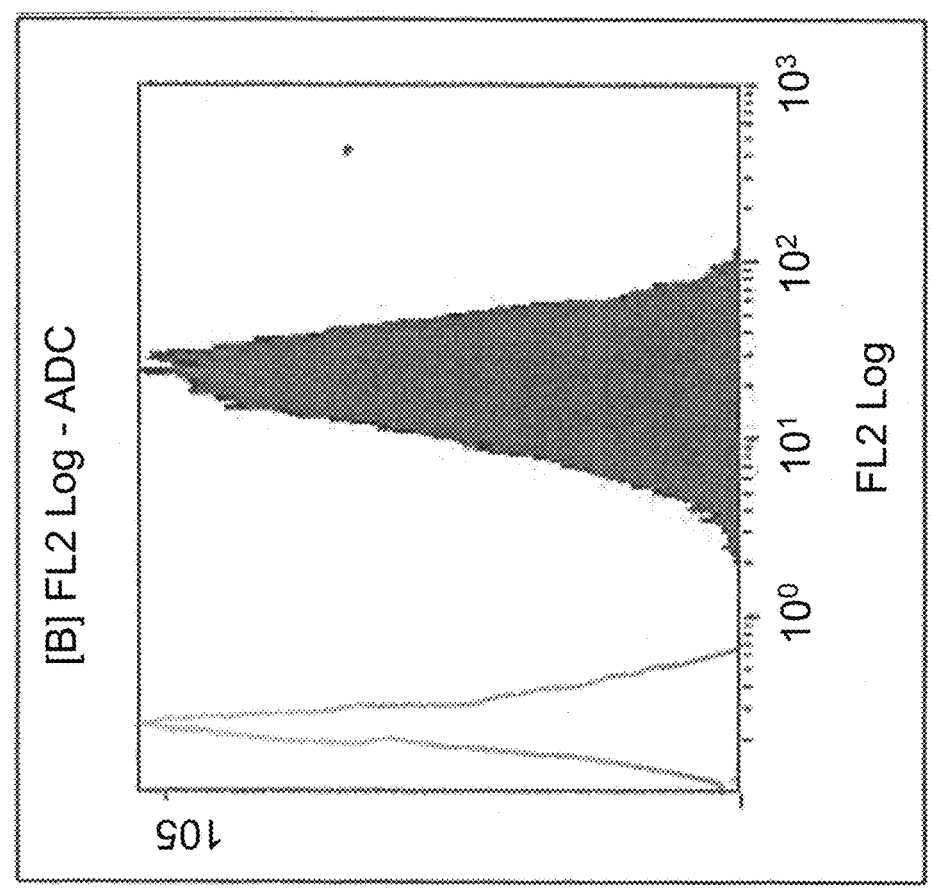
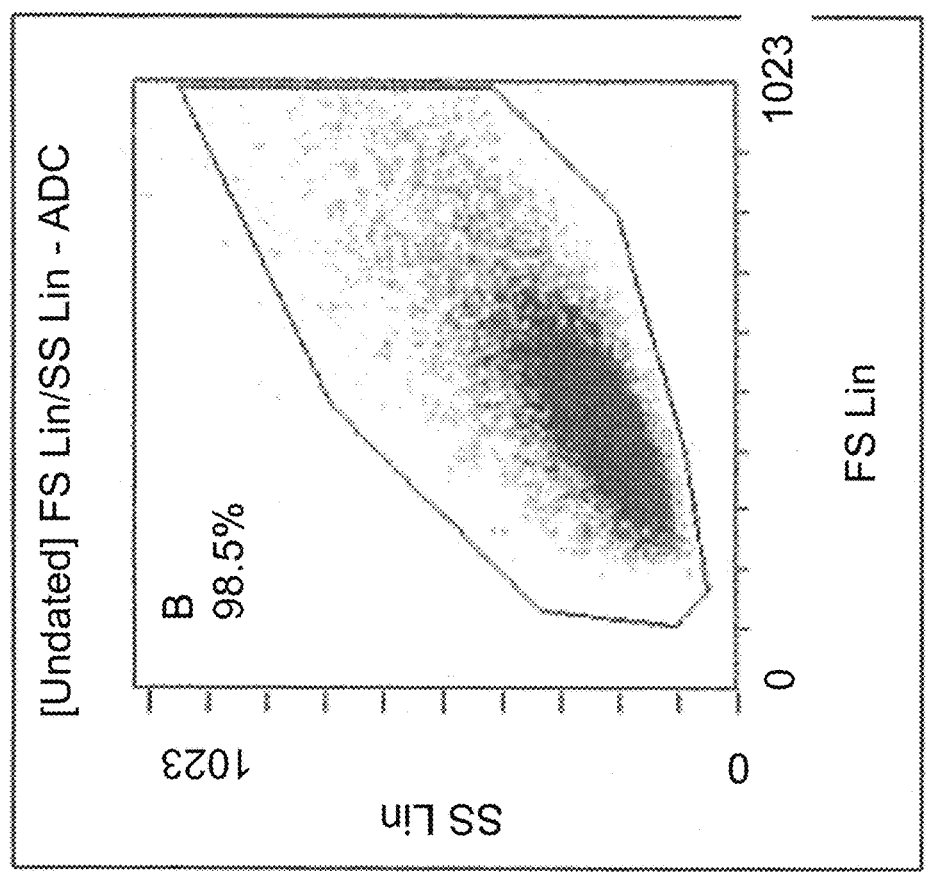

FIG. 10A
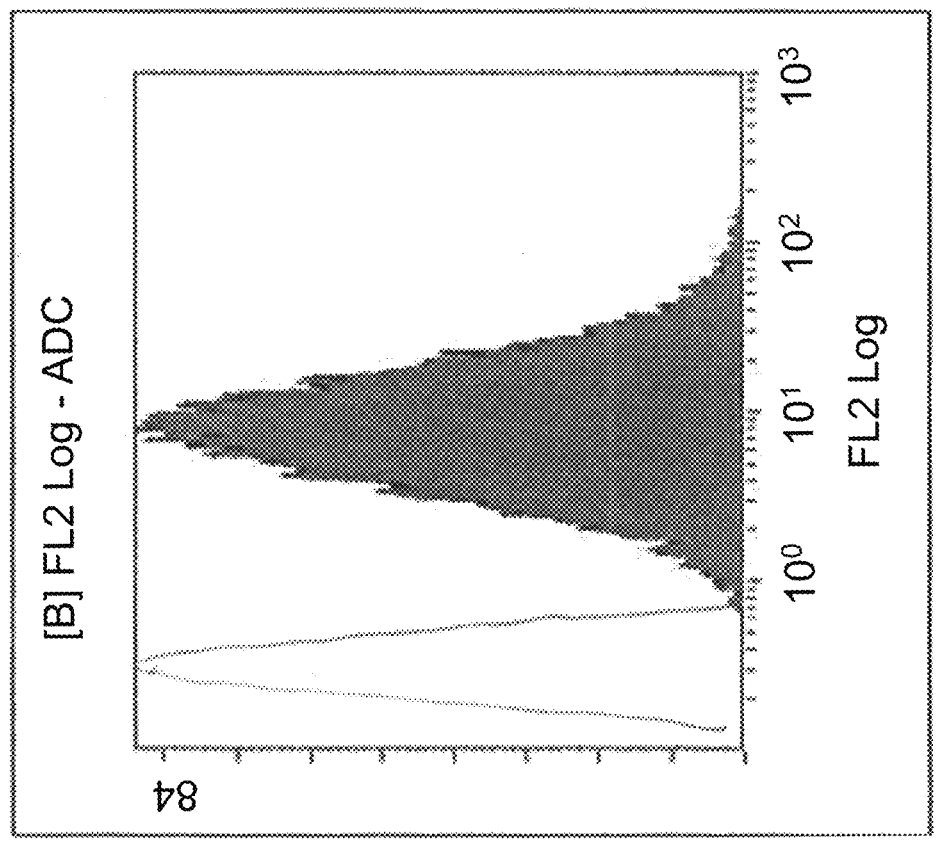
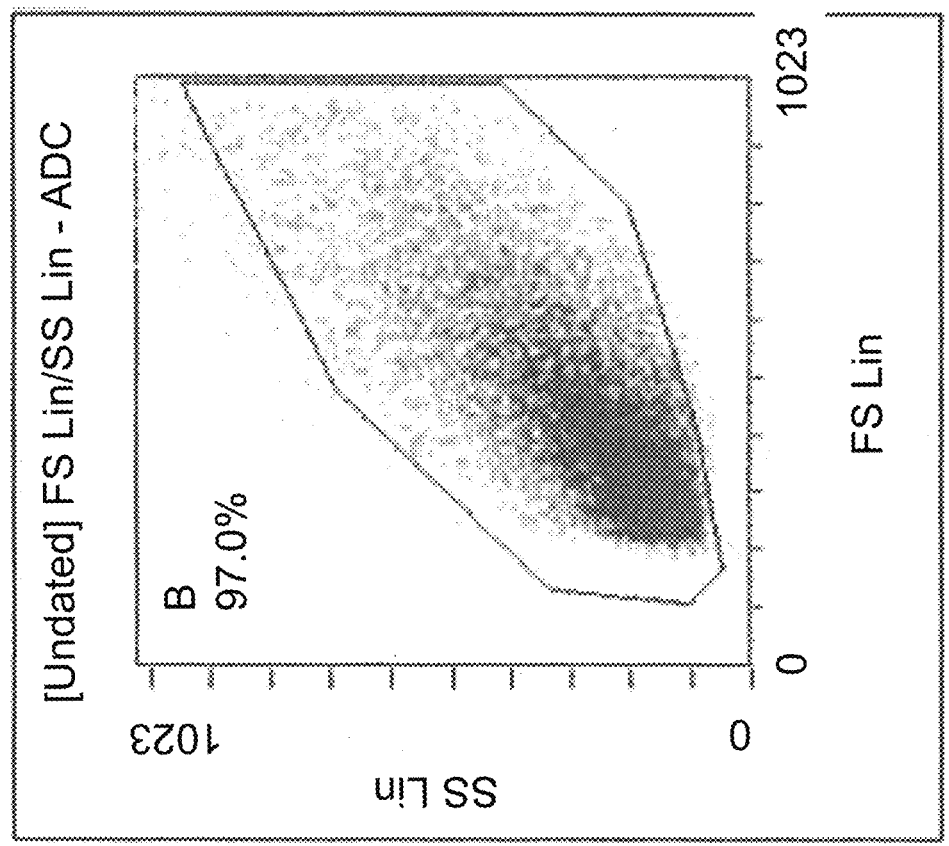

METHOD FOR DETECTING LIPID BILAYER MEMBRANE PARTICLES OR FRAGMENTS THEREOF

CROSS-REFERENCE TO RELATED APPLICATION

The present application claims priority under 35 U.S.C. § 119 to Japanese Patent Application No. 2017-081568, filed Apr. 17, 2017, and Japanese Patent Application No. 2017-129524, filed Jun. 30, 2017. The contents of these applications are incorporated herein by reference in their entirety.

BACKGROUND

The present disclosure relates to a method for detecting lipid bilayer membrane particles or fragments thereof.

Hitherto, it has been known that cells release vesicles during apoptosis; however, it has been revealed that healthy cells also release vesicles similarly, and thus the physiological functions of the vesicles have attracted attention. Such extracellular vesicles (EVs) are derived from cells and thus have the form of particles covered with lipid bilayer membranes (lipid bilayer membrane particles; lipid vesicles), but it is found that there are several types of extracellular vesicles depending on derivations or characteristics thereof.

First, "apoptotic bodies (ABs)" are vesicles released from apoptotic cells, have a size of about 1000 to 4000 nm (1 to 4 μm) due to occurrence mechanism thereof, and serve functions such as induction of phagocytosis.

Meanwhile, both "microvesicles (MVs)" and "exosomes" are vesicles released from normal cells and discriminated from each other on the basis of the occurrence mechanism. Specifically, extracellular vesicles formed or secreted by sinking of membranes of multivesicular bodies (MVBs) in the inside thereof are defined as exosomes and the size thereof is about 30 to 200 nm. The exosomes contain a large number of Alix, Tsg101 and HSP70, which are endosome-binding proteins, and tetraspanin families (CD63, CD81, and CD9), which are membrane-spanning proteins, or the like. Thus, these proteins are used as exosome marker molecules in detection of exosomes in a sample derived from a living body. Further, regarding exosomes extracted using these molecules as markers, analysis of microRNA (miRNA) and the like contained therein has been conducted, and currently, comprehensive search tests for leading to cancer treatment have been advanced as a national project.

In contrast with the exosomes, extracellular vesicles budded directly from cell membranes (ectosomes) are defined as microvesicles (MVs). The microvesicles (MVs) are generated by fragmentation of a cell skeleton due to flip flop phenomenon of two occurrence mechanisms of microparticles (MPs), and thus the size thereof is about 100 to 1000 nm. The microvesicles contain a large number of proteins, nucleic acids, miRNAs, which are derived from cells (Annexin V, integrin, selectin, CD40 ligand, and metalloproteinase), and the like. These exosomes and MVs serve functions such as cell-to-cell communication. The ectosomes contain a large number of tissue factors (CD142: TFs), which are transmembrane proteins, and the like. Regarding markers of MVs or MPs, a surface antigen marker or the like of a parent cell serving as an expression origin is used together with size information and an activation marker, and for example, markers that are derived from vascular endothelial cells, monocytes, blood platelets, and the like have attracted attention.

Further, besides the aforementioned extracellular vesicles, circulating tumor cells (CTCs), circulating endothelial cells (CECs), and circulating endothelial progenitors (CEPs) are known as lipid vesicles that circulate in peripheral bloods in accordance with progression (metastasis or the like) of disease state of cancer. Since these are cells, similarly to the lipid vesicles, these cells have the form of particles covered with lipid bilayer membranes (lipid bilayer membrane particles).

The circulating tumor cells (CTCs) are defined as tumor cells that circulate in a peripheral blood flow of a cancer patient and are tumor cells that are invaded from a primary tumor or a metastatic tumor into blood vessels. Detection of the CTCs has recently attracted attention as one of methods for early detection of metastatic malignancy. The reason for this is that the detection of the CTCs is less invasive than detection using X-ray photography or a tumor marker in the blood serum and enables the diagnosis of metastatic malignancy to be precisely performed, and can be used as a barometer of prognostic prediction or treatment effect of patients.

Further, the circulating endothelial cells (CECs) are defined as mature cells peeled away from blood vessel walls due to natural metabolism of endothelial cells, and serve functions of vascularization and maintaining the blood vessel walls. It has been reported that the CECs increase in a large number of disease states of cardiovascular diseases, infective diseases, immunological diseases, tests after transplant, cancers, and the like. In particular, in cancer researches, the CECs are suggested as a non-invasive biomarker of angiogenic activity showing tumor regrowth, resistance to chemotherapy, early recurrence, and metastasis during or after chemotherapy. Meanwhile, it has been reported that the CEC level in healthy individuals is extremely low and is about 0.01 to 0.0001% of whole peripheral blood mononuclear cells.

Furthermore, it has been known that the circulating endothelial progenitors (CEPs) exist in peripheral blood mononuclear cell fractions of adults and the endothelial progenitors are locally grown and differentiated so that they involve in vascularization. The CEPs are recruited from the bone marrow even at the time of construction of new blood vessels in the case of cancers and are circulated in blood at the time of newly creating blood vessels according to metastasis of cancer. For these reasons, the CEPs are expected as a non-invasive biomarker similar to the CECs. Further, these CECs and CEPs are also studied for being used as a marker for determining the treatment effect of antibody drugs and presence/absence of adverse events.

All of the lipid bilayer membrane particles of extracellular vesicles, CTCs, CECs, CEPs, and the like described above are detected in blood circulating in a living body. For this reason, there is an advantage in that by detecting these lipid bilayer membrane particles in a blood sample derived from the living body, abnormity in the living body can be detected without performing an invasive biopsy test.

As a method for detecting such lipid bilayer membrane particles, conventionally, a substance which specifically binds to a surface antigen existing on surfaces of the lipid bilayer membrane particles (hereinafter referred to as "specifically-binding substance") such as an antibody or the like is caused to emit light using a fluorescence probe labeled with a fluorescent dye so as to be detected by flow cytometry or imaging cytometry (for example, see JP 2012-168012 A). Herein, the amount of the above-described lipid bilayer membrane particles existing in the sample is extremely scarce depending on circumstances. Further, for example, in the case of describing CTCs as an example, it is known that the lipid bilayer membrane particles exist in an amount corresponding to only about one cell of $10^9$ to $10^{10}$ cells/mL of blood cells contained in blood of a metastatic cancer patient. In order to ensure the amount of the surface antigen for the purpose of enabling such a scarce detection target to be sufficiently measured, it is necessary to measure an extremely large number of particles (vesicles) also including particles (vesicles) serving as a noise source. However, since there is limitation on the number of measurable particles, a sufficient measurement number cannot be typically ensured, and thus, it is not possible to sufficiently increase detection sensitivity only by increasing the measurement number. For the purpose of condensing a scarce detection target in this way, a method has been known in which an antibody or the like that specifically binds to a detection target is conjugated with a magnetic bead, and then the detection target is condensed by a separation operation using a magnetic apparatus (a magnet) (for example, see JP 2013-015517 A).

Further, for the purpose of observing the forms of the lipid bilayer membrane particles (lipid vesicles) or observing the states of localized lipid (granules, cell vesicles, mitochondria, or the like) inside the particles (vesicles), a technique has been known in which a lipid bilayer membrane is stained using a fluorescent dye staining a lipid bilayer membrane (so-called lipid staining) (for example, see JP 2014-236685 A). Incidentally, a technique of using this lipid staining in combination with the aforementioned separation and detection method using flow cytometry or the like has not been known in the related art. For example, in Yusuke Yoshioka, Takahiro Ochiya, "Exosome provides new insight into liquid biopsy", Cytometry Research, Japan Cytometry Society, Vol. 26 (2016) No. 1, pp. 1-6, a technique has been reported in which a protein existing on an exosome membrane is sandwiched by two types of monoclonal antibodies on which different modifications are conducted (one is a biotinylated antibody to which Alpha donor bead covered with streptavidin binds and the other is an antibody to which AlphaLISA acceptor bead is allowed to bind) (ExoScreen method). In this technique, only in a case where two types of antibodies come close within 200 nm, singlet oxygen generated by excitation of a photosensitizer contained in the donor bead undergoes chemiluminescence reaction with the acceptor bead to generate a fluorescence signal, so that the exosomes can be detected by measuring this fluorescence signal.

SUMMARY

The fluorescence intensity of the fluorescence probe depends on the amount of an antigen existing on surfaces of the lipid bilayer membrane particles in theory. Further, since the size of the aforementioned lipid bilayer membrane particles is extremely small and the amount of the surface antigen is also extremely small due to the small area of the particles, the intensity of fluorescence derived from the lipid bilayer membrane particles serving as a measurement target is typically weak. Meanwhile, cells or lipid vesicles that are not a detection target are also contained in the measurement sample, and background fluorescence derived from these cells or lipid vesicles that are a non-detection target (auto-fluorescent light, fluorescence caused by non-specific reaction of the fluorescent dye, or the like) exists. For this reason, the intensity of the fluorescence derived from the lipid bilayer membrane particles serving as a detection target is equal or less than the intensity of the background fluorescence in some cases, and in this case, a problem arises in that the lipid bilayer membrane particles serving as a detection target cannot be detected. Incidentally, this problem cannot be resolved even by using the fluorescence probe conjugated with the magnetic bead as described above as long as the fluorescence intensity depends on the amount of the surface antigen in which the amount of the surface antigen existing on the surfaces of the lipid bilayer membrane particles is very small.

In this regard, an object of the present disclosure is to provide a means by which a signal-to-noise ratio (S/N ratio) can be improved at the time of detection of lipid bilayer membrane particles (lipid vesicles or cells) in which the amount of a surface antigen is small since the size of the particles is small and/or the amount of the particles existing in a sample is also small.

The present inventors have conducted intensive studies in view of the above-described problems. As a result, they have found that the above-described problems can be solved by concurrently using a lipid staining method and a separation and detection method that uses a specifically-binding substance such as an antibody, that have not been used in combination in the related art, at the time of detection of lipid bilayer membrane particles or fragments thereof, thereby completing the present disclosure.

That is, according to the first aspect of the present disclosure, there is provided a method for detecting lipid bilayer membrane particles or fragments thereof having predetermined molecules existing on surfaces in a biological sample collected from a subject, the method including:

adding a dye staining a lipid bilayer membrane to the biological sample;

adding a substance specifically binding to the predetermined molecules to the biological sample;

trapping the substance to separate the lipid bilayer membrane particles or fragments thereof having predetermined molecules existing on surfaces; and detecting the separated lipid bilayer membrane particles or fragments thereof on the basis of emission of the dye.

It is preferable that the specifically-binding substance according to the first aspect contain a magnetic bead or be capable of binding to a magnetic bead, and the trapping of the specifically-binding substance be performed by using a magnetic apparatus. Further, in a case where the specifically-binding substance contains a magnetic bead, it is preferable that the specifically-binding substance bind to the magnetic bead. On the other hand, in a case where the specifically-binding substance is capable of binding indirectly to the magnetic bead, it is preferable that the specifically-binding substance be labeled with biotin, and the magnetic bead be labeled with avidin or a derivative thereof or an anti-biotin antibody which is bindable to biotin. Further, in a case where the specifically-binding substance can directly bind to the magnetic bead, the specifically-binding substance can bind to the magnetic bead by functional group modification of the magnetic bead. Furthermore, in a case where the magnetic bead is used, it is preferable that the magnetic bead be subjected to a blocking treatment.

It is preferable that the specifically-binding substance according to the first aspect be an antibody or an engineered antibody, and it is preferable that the specifically-binding substance be not labeled with a fluorescent dye.

It is preferable that the predetermined molecule according to the first aspect be a membrane protein, and the membrane protein be one or more of CD antigens selected from the group consisting of CD63, CD81, CD9, CD82, CD151, CD326, CD144, CD105, CD146, CD62E, CD142, CD41a, CD62P, CD61, CD11b, CD32, CD33, CD14, CD66b, CD56, CD16, and CD64.

In the first aspect, it is preferable that detection of the lipid bilayer membrane particles or fragments thereof be performed by flow cytometry or imaging cytometry. At this time, it is preferable that fluorescence intensities of fluorescences of two or more colors having a different fluorescence wavelength be measured by using a plurality of channels in the detection of the lipid bilayer membrane particles or fragments thereof.

BRIEF DESCRIPTION OF THE DRAWINGS

FIG. 1 is an explanatory diagram for describing an example of a specific method of performing, by flow cytometry, quantitative determination of particles (fragments) in microparticle (MP) areas of lipid bilayer membrane particles or fragments thereof detected by a detection method according to the present disclosure.

FIG. 3A is a stained lipid sample; FIG. 3B is a non-stained lipid sample.

FIG. 4 is a stained lipid sample; FIG. 4B is a non-stained lipid sample.

FIG. 5A, with added anti-CD326 antibody labeled with Fluor 647 (emission at 575 nm); FIG. 5B, without the labeled anti-CD326 antibody.

FIG. 6A presents measurement results of a positive control; FIG. 6B presents measurement results of a negative control.

FIG. 8A, stained lipid sample; FIG. 8B, non-stained lipid sample.

FIGS. 9A and 9B are diagrams showing a first plot and a sixth plot obtained by measuring A431 cells by flow cytometry: FIG. 9A, stained lipid sample; FIG. 9B, non-stained lipid sample.

FIGS. 10A and 10B is diagrams showing a first plot and a sixth plot obtained by measuring PC3 cells by flow cytometry: FIG. 10A, stained lipid sample; FIG. 10B, non-stained lipid sample.

FIG. 11A shows a plot of side scattered light (SS) versus forward scattered light (FS); FIG. 11B shows a plot of fluorescence intensity of the first fluorescence wavelength (FL1) of the dye versus the second fluorescence wavelength (FL2).

FIG. 12A shows a plot of side scattered light (SS) versus forward scattered light (FS); FIG. 12B shows a plot of fluorescence intensity of the first fluorescence wavelength (FL1) of the dye versus the second fluorescence wavelength (FL2).

FIG. 13A shows a plot of side scattered light (SS) versus forward scattered light (FS); FIG. 13B shows a plot of fluorescence intensity of the first fluorescence wavelength (FL1) of the dye versus the second fluorescence wavelength (FL2).

DETAILED DESCRIPTION

Figure 2A:
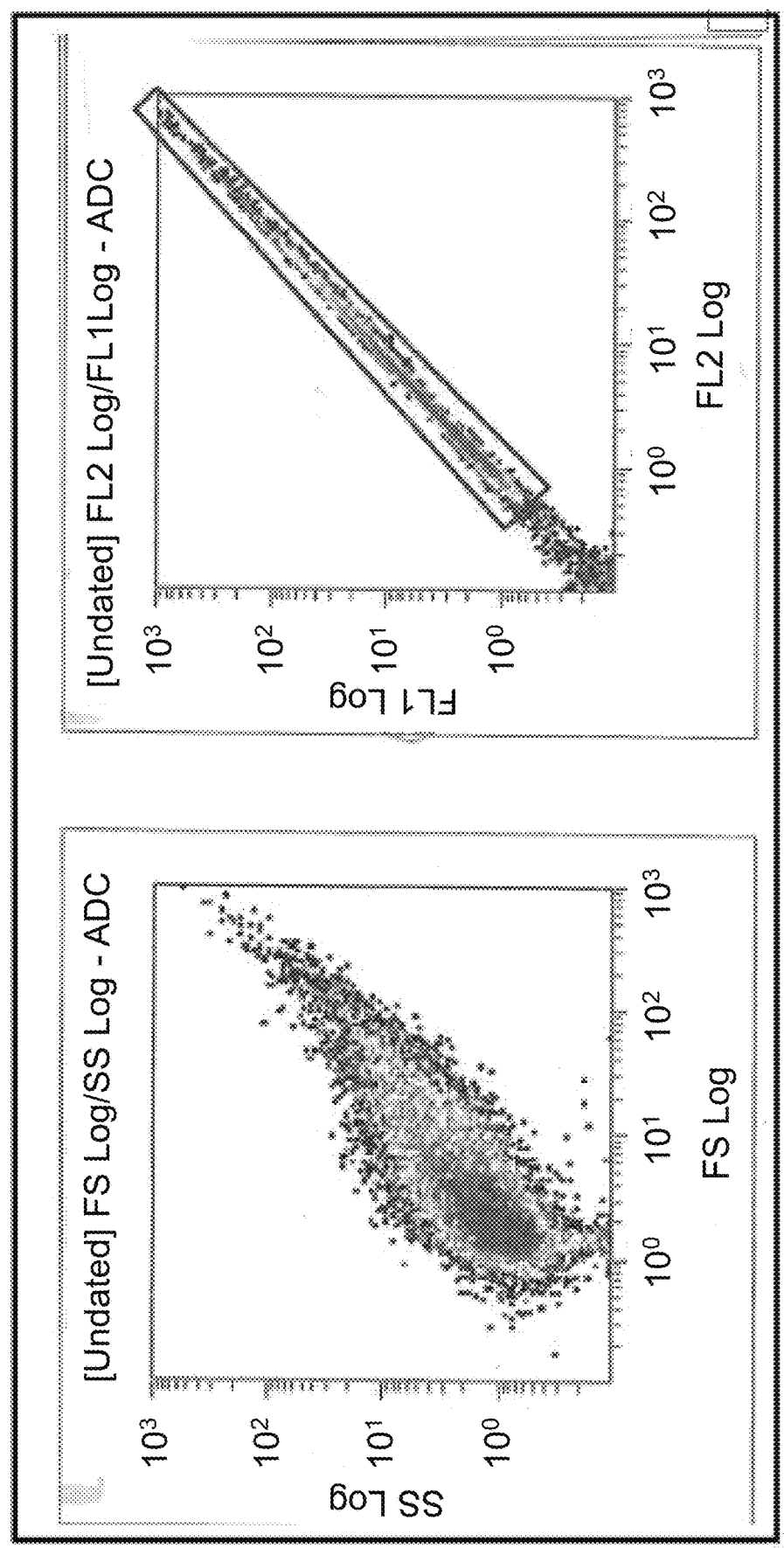
FIG. 2A is a diagram showing the flow cytometry measurement results of artificial lipid bilayer membrane vesicles (artificial liposome, DMPC: dimyristoylphosphatidylcholine) subjected to lipid staining by the method of the present disclosure.

Embodiments of the present disclosure will be described below with reference to the accompanying drawings.

The first aspect of the present disclosure relates to a method for detecting lipid bilayer membrane particles or fragments thereof having predetermined molecules existing on surfaces in a biological sample collected from a subject. Herein, the detection method according to the aspect has a feature in that the method includes adding a dye staining a lipid bilayer membrane to the biological sample (dye addition step), adding a substance specifically binding to the predetermined molecules (specifically-binding substance) to the biological sample (specifically-binding substance addition step), trapping the substance to separate the lipid bilayer membrane particles or fragments thereof having predetermined molecules existing on surfaces (separation step), and detecting the separated lipid bilayer membrane particles or fragments thereof on the basis of emission of the dye (detection step).

According to the present disclosure, it is possible to improve a signal-to-noise ratio (S/N ratio) at the time of detection of lipid bilayer membrane particles (lipid vesicles) in which the amount of a surface antigen is small since the size of the particles is small and/or the amount of the particles existing in a sample is also small.

Hereinafter, preferred embodiments for carrying out the detection method according to this aspect will be described in detail by using a case where detection of the lipid bilayer membrane particles or fragments thereof is performed by a flow cytometry method as an example; however, the scope of the present disclosure should be defined on the basis of the scope of claims and is not limited only to the following specific embodiments.

(Dye Addition Step)

As described above, in the detection method according to the present aspect, a biological sample collected from a subject is used as a sample serving as a measurement target. Further, in this step, a dye staining a lipid bilayer membrane is added to the biological sample collected from the subject.

As used herein, the "subject" is not particularly limited as long as it is an animal, and examples thereof include mammals. Examples of the mammals include primates, laboratory animals, domestic animals, and pets and there is no particular limitation on the mammals. Specific examples thereof include humans, monkeys, rats, mice, rabbits, horses, cows, goats, sheep, dogs, and cats. Preferably, the subject is human. In another embodiment, in a case where the detection target is CTC, CEC, or CEP, the subject is preferably an animal that has a probability of being affected with cancer, and this is preferably applied to human. The detection method according to this aspect is particularly preferably performed on a human that is suspected to be affected with cancer, a human that was affected with cancer, or the like.

Further, the biological sample to be used in the detection method according to this aspect is not particularly limited, and biological samples that are generally used in conventional clinical inspection maybe used. Examples of the biological sample include tissues, cells, cell extracts, and body fluids that are derived from the animal serving as the subject. Examples of the tissues include those of a spleen, lymph node, kidney, lung, heart, and liver, examples of the cells include splenocytes, lymphocytes, neutrophils, monocytes, macrophages, dendritic cells, and antibody-producing cells, and examples of the body fluids include ascites fluid, celomic fluid, urine, sweat, and spinal fluid in addition to a blood sample. Among these, the biological sample is preferably a blood sample, ascites fluid, or celomic fluid and more preferably a blood sample.

The "blood sample" is not particularly limited as long as the lipid bilayer membrane particles or fragments thereof can be detected in a case where the lipid bilayer membrane particles or fragments thereof are contained in the blood sample. For example, pellets obtained by dissolving erythrocytes in the blood sample and then performing separation by centrifugation to remove the supernatant may be used. Further, it is also preferable to use centrifugation supernatant obtained by centrifugation treatment as described later. Incidentally, there is no particular limitation on timing for collecting a blood sample from the subject.

Incidentally, since many blood cell components exist in a whole blood sample as compared with microparticles such as circulating cells of EVs, CTCs, and the like, in the detection method of the present disclosure, it is preferable to use a plasma sample rather than the whole blood sample as the blood sample. Specifically, it is necessary to remove the blood cell components as gently as possible, particularly, to avoid contamination of blood platelets as much as possible, so that excessive microparticles may not be produced from blood cells in the treating process of the whole blood sample. To remove the blood cell components from the whole blood sample and to obtain a plasma sample, plasma components may be separated by centrifugation. Incidentally, there is no particular limitation on the condition of centrifugation. For example, in a case where blood platelets of blood cell components, which are the smallest component, are separated, a method may be used in which plasma components are obtained by centrifugation at 3000 rpm (1710×g) for 10 minutes, and then centrifugation is performed in such a condition at 8000×g for 5 minutes, which is the simplest method, thereby obtaining a sample from the supernatant. Further, in a case where cell vesicles that are to be precipitated in this condition are detected, it is also effective to alleviate the centrifugation condition and select centrifugation at 500×g for 10 minutes. Furthermore, in a case where condensation of the supernatant sample is necessary, for example, it is also effective to perform centrifugation at 20000×g for 60 minutes so as to use a pellet part as the target sample.

Further, it is also effective to perform negative selection or positive selection on cell vesicles, which are nota measurement target, by utilizing a column or a minute fluidic circuit without use of the centrifugation operation and by using a size or an antibody marker, or the like. Incidentally, a microtube made from polypropylene may be used as a sample container.

Further, in order to detect microparticles which exist at the time of blood collection and to make the microparticles not to be expressed after blood collection, it is important not to make blood platelets activated. Therefore, in the occasion of preparing a blood sample such as a plasma sample, it is preferable to use citric acid or EDTA, which has Ca ion chelating activity, as an anticoagulant. Incidentally, conventionally, the measurement of MPs has been performed generally by using a citric acid blood collection tube; however, in a case where the object is to detect only the lipid bilayer membrane particles or fragments thereof, for the purpose of improving sample stability, it is more preferable to use EDTA, which has strong Ca ion chelating effect, as an anticoagulant. Incidentally, in the case of performing the centrifugation operation, it is also considered that by suppressing expression of cell vesicles and the like due to the activation of the blood cell components which are contained concurrently or by promoting coagulation in the process of preparing a sample, the cell vesicles are introduced into a fibrin clot or the like so that the cell vesicles do not remain in the centrifugation supernatant serving as a collection source for a target sample. For this reason, it is also effective to add an anticoagulant such as EDTA, as necessary, after the first centrifugation treatment is performed.

Regarding the biological sample to be used in the detection method according to the present disclosure, a biological sample immediately after being collected from a subject is preferably used for measurement, but a stored biological sample maybe used. A method for storing the biological sample is not particularly limited as long as it is performed in such a condition that the amount of the lipid bilayer membrane particles or fragments thereof in the sample does not change, and for example, the storing method is preferably performed under a low-temperature condition of 0 to 10° C., at which freezing does not occur, a dark condition, and a condition without vibration.

The method according to the present disclosure is to detect the "lipid bilayer membrane particles or fragments thereof having predetermined molecules existing on surfaces" contained in the biological sample as a detection target. Herein, there is no particular limitation on the "lipid bilayer membrane particles or fragments thereof having predetermined molecules existing on surfaces" and it is sufficient that the lipid bilayer membrane particles or fragments thereof having predetermined molecules existing on surfaces are lipid bilayer membrane particles or fragments thereof having predetermined molecules existing on surfaces which can bind to a specifically-binding substance to be described later. As such lipid bilayer membrane particles serving as a detection target, first, the aforementioned extracellular vesicles (EVs) such as apoptotic bodies (ABs), microvesicles (MVs), and exosomes are exemplified. Further, similarly, the aforementioned circulating cells such as circulating tumor cells (CTCs), circulating endothelial cells (CECs), and circulating endothelial progenitors (CEPs) are also exemplified as the lipid bilayer membrane particles serving as a detection target. There is no particular limitation on the size of the lipid bilayer membrane particles or fragments thereof serving as a detection target, and any sizes are applicable as long as it is a size which can be detected. Incidentally, the typical size of the extracellular vesicles (EVs) are as described above; however, the size of various circulating cells are generally about 6 to 10 μm, for example, in the case of CTCs (in the case of cultured cancer cells, generally about 10 to 16 μm).

In the detection method according to the present disclosure, it is necessary that "predetermined molecules" that can bind to a specifically-binding substance to be described later exist on surfaces of the lipid bilayer membrane particles or fragments thereof serving as a detection target. Specific embodiments of the "predetermined molecules" are also not particularly limited as long as they can bind to the specifically-binding substance to be described later, but the "predetermined molecule" is preferably a membrane protein. Further, the membrane protein is preferably a cell surface antigen referred to as a so-called CD antigen, and according to such an embodiment, antibodies or engineered antibodies in accordance with classification of various types of CDs can be used as the specifically-binding substance. In a case where the predetermined molecule is a membrane protein that is a CD antigen, the membrane protein is preferably one or more of CD antigens selected from the group consisting of CD63, CD81, CD9, CD82, CD151, CD326, CD144, CD105, CD146, CD62E, CD142, CD41a, CD62P, CD61, CD11b, CD32, CD33, CD14, CD66b, CD56, CD16, and CD64. Herein, CD326 is called an epithelial cell adhesion molecule (EpCAM) and is conventionally used in detection of CTCs. CD144 (cadherin 5, VE-cadherin), CD105 (endoglin), CD146 (S-Endo, Endo-CAM), CD62E (E-selectin), and the like are known as a membrane protein (surface antigen) existing on surfaces of vascular endothelial cell-derived microparticles (EDMPs). CD142 exists on surfaces of tissue factor-containing microparticles (TFs). CD41a (GPIIb/IIIa), CD62P, and CD61 are blood platelet-specific receptors and exist on surfaces of blood platelet-derived microparticles (PDMPs). CD11b (integrinαM chain, Mac-1), CD32, CD33, and CD14 are known as a macrophage marker and exist on surfaces of monocyte-derived microparticles (MDMPs). CD66b, CD56, CD16, and CD64 exist on surfaces of neutrophil-derived microparticles (NDMPs). Incidentally, as the "predetermined molecule", other than the CD antigens as described above, receptor proteins, adhesion molecules, proteins such as enzymes, sugar chains binding to proteins, and the like may be used.

In particular, markers that are relevant to treatment, prognosis monitoring, prevention, anticipation, and the like of a cancer patient are as follows.

A large number of tissue factors (CD142: TFs) that are transmembrane proteins, CD144, and the like are contained in ectosomes. Thus, these proteins are used as marker molecules of exosomes in a sample derived from the living body. Formation and fibrinolysis of thrombi are constantly repeated even in blood vessel walls that are not subjected to invasion, and if a balance between thrombotic tendency and hemorrhagic tendency is disrupted, various disorders are caused. In particular, in the case of a cancer patient, this balance becomes extremely unstable. For this reason, it is reported that, in order to maintain homeostasis, a large number of EVs having TFs (CD142) exist in the peripheral blood. In neoplastic cell-derived ectosomes, there are large vesicles (LV; or LO; oncosomes), and these vesicles have a size of about 2000 to 50000 nm (2 to 50 μm) due to occurrence mechanism thereof and serve the function of transporting a carcinogenic material, and the like. Meanwhile, neoplastic cell-derived exosomes and ectosomes can produce ABs, and serve functions such as cell-to-cell communication with a target cell. In a large number of hematological disorders, procoagulant activity (PA) is recognized. As main hematological disorders, idiopathic thrombocytopenic purpura (ITP; immune thrombocytopenia), antiphospholipid antibody syndrome (APS), thrombotic thrombocytopenic purpura (TTP), heparin-induced thrombocytopenia (HIT), disseminated intravascular coagulation (DIC), paroxysmal nocturnal hemoglobinuria (PNH), acute myeloid leukemia (AML), multiple myeloma (MM), chronic lymphocytic leukemia (CLL), chronic myelogenous leukemia (CML), stem cell transplantation (SCT), hematopoietic stem cell transplantation (HSCT), and the like are reported. Among these hematological disorders, in DIC, AML, MM, CLL, CML, SCT, and HSCT, expression of the tissue factors (CD142: TFs) is recognized.

From the above description, as a marker relevant to treatment, prognosis monitoring, prevention, anticipation, and the like of a tissue-derived cancer patient, CD142 and CD326 are preferably used as essential markers together with those conventionally used in detection of CTCs.

Further, regarding exosomes, CD9 that is a tetraspanin family molecule activates an enzyme ADM17, CD63 activates integrin, and CD81 activates EGFR and is relevant to Recomodulin. In particular, CD63, CD81, and CD9 are CD antigens belonging to the tetraspanin family and have the function of activating other proteins by forming complexes with other membrane proteins. Further, in the present disclosure, these CD antigens are suitably used particularly in the detection of exosomes. Furthermore, CD63 among these does not exist extracellularly in general cells so that the activation of cells can be detected by performing detection using the CD63 antigen as a marker. For these reasons, selecting these three types of antigens as a marker corresponds to another preferred embodiment. Since CD63 is expressed in lysosomal granules, typically, CD63 does not exist extracellularly. So, if not in EVs, CD63 does not exist extracellularly. Further, since CD9 is also expressed in blood platelets, it may be necessary to use CD9 in combination with another marker or to perform identification on the basis of the size. Thus, it is preferable that CD63 be used as an essential marker and be necessarily used in combination with CD81.

In this step, there is no particular limitation on the "dye staining a lipid bilayer membrane" added to the biological sample, and a lipid-soluble dye that has been conventionally used in so-called lipid staining may be similarly used. The "lipid staining" is a method of staining a lipid bilayer membrane using a lipid-soluble dye by using the property that the dye is dissolved in lipid. This lipid staining has no connection with an ionic function group unlike other staining methods, and is a method in which a dye that is insoluble in water and has high lipid affinity is allowed to act on lipid to impregnate the dye into a lipid bilayer membrane to thereby stain the lipid bilayer membrane. Examples of such a lipid-soluble dye include a lipid-soluble carbocyanine dye SP-DiOC$_{18}$ (3) of Molecular Probes (registered trademark) series manufactured by Thermo Fisher Scientific, and Polaric (registered trademark) manufactured by GORYO Chemical, Inc., these dyes can be excited by using general blue laser of 488 nm, and the dyes emit light of the maximum fluorescence wavelength which is shifted to the long-wavelength side. Further, in addition thereto, lipid-soluble dyes such as Sudan III, Sudan II (oil red O), Sudan Black B (SBB), Nile blue, Fat Red, and Lipid Crimson that have been conventionally used in the lipid staining may also be used similarly. Incidentally, the amount of the dye added to the biological sample is not particularly limited, and can be appropriately determined with reference to conventionally known knowledge.

(Specifically-Binding Substance Addition Step)

In this step, a substance specifically binding to the aforementioned predetermined molecules (specifically-binding substance) is added to the biological sample. According to this, in the separation step to be described later, it is possible to separate the lipid bilayer membrane particles or fragments thereof having predetermined molecules existing on surfaces.

Incidentally, this step maybe performed before, at the same time of, or after the aforementioned "dye addition step". Particularly, from the viewpoint of reducing the influence of lipid staining on antibody binding reaction, this step (specifically-binding substance addition step) is preferably performed before the dye addition step. Further, after the antibody binding reaction is terminated by this step, it is more preferable to carry out a washing step and then carry out a lipid staining step. Furthermore, it is particularly preferable to further carry out the washing step after the lipid staining step.

It is necessary that "(1) the "specifically binding substance" used in this step binds specifically to predetermined molecules existing on surfaces of the lipid bilayer membrane particles or fragments thereof serving as the detection target". Further, it is also necessary that "(2) the "specifically-binding substance" can separate only the lipid bilayer membrane particles or fragments thereof having the predetermined molecules existing on the surfaces thereof by using the specifically-binding substance as a probe in the separation step to be described later and specifically trapping the specifically-binding substance".

Regarding the specifically-binding substance for satisfying the above condition (1), an antibody, an engineered antibody, an aptamer, a ligand molecule, ligand mix, an inhibitor competitive with binding to ligand, an extracellular matrix or adhesion factor binding to an adhesion molecule, mimics thereof, a matrix with respect to an enzyme, an inhibitor with respect to the enzyme, a substance having an allosteric effect with respect to the enzyme, lectin binding to a sugar chain, and the like are exemplified. Examples of the antibody include IgG, IgA, IgD, IgE, and IgM. Incidentally, the antibody is preferably a monoclonal antibody. Herein, examples of IgG include IgG1, IgG2, IgG3, and IgG4. Examples of IgA include IgA1 and IgA2. Examples of IgM include IgM1 and IgM2. Examples of the engineered antibody include Fab, F(ab')2, and scFv. Examples of the aptamer include a peptide aptamer and a nucleic-acid aptamer. Examples of the ligand molecule include ligands of receptor proteins in a case where the predetermined molecules existing on surfaces of the lipid bilayer membrane particles or fragments thereof are receptor proteins. For example, in a case where the molecule existing on the surface of the exosome is interleukin, G protein and the like are exemplified as the ligand molecule. Among these, an antibody or an engineered antibody is preferable as the specifically-binding substance. Further, in a case where the specifically-binding substance is an antibody or an engineered antibody, the specifically-binding substance is an antibody or an engineered antibody that specifically binds to the predetermined molecules existing on the surfaces of the lipid bilayer membrane particles or fragments thereof serving as a detection target. For example, in a case where the lipid bilayer membrane particles serving as a detection target are CTCs, the predetermined molecule is CD326 protein (EpCAM) and thus an anti-CD326 antibody may be used as the specifically-binding substance.

Incidentally, the specifically-binding substance may be labeled with a direct labeling substance. In the case of the indirect labeling substance, for example, charged molecules of biotin, avidin or a derivative thereof (streptavidin, neutravidin, or the like), glutathione-S-transferase, glutathione, a fluorescent dye, polyethylene glycol, mellitic acid, and the like are exemplified. However, in the present disclosure, in the case of a tandem dye, there may be troubles that non-specific reaction often occurs or the emission wavelength caused by the non-specific reaction overlaps the detection wavelength unless the specifically-binding substance has a different wavelength from that of the orthochromatic dye. For this reason, the specifically-binding substance is preferably not labeled with a fluorescent dye.

Further, for satisfying the above condition (2), the specifically-binding substance has the property of being specifically trapped in the separation step to be described later. Specifically, the separation step is typically performed by trapping, using a solid phase, specific lipid bilayer membrane particles or fragments thereof, which are desired to be separated, and removing particles (fragments) that are not trapped. Herein, the "solid phase" is a solid-like or gel-like carrier to be used in the step of separating specific lipid bilayer membrane particles or fragments thereof, and indicates one which can be easily separated with respect to a liquid phase. As an example of the solid phase, for example, plastic, rubber, insoluble polysaccharides, (insoluble) silicon compounds, and the like are exemplified, but the solid phase is not limited thereto. Further, any forms of the solid phase may be employed as long as it is a form in which the solid phase can be easily separated from a liquid phase, but in order to increase a surface area ratio, a particulate form is preferably employed. Furthermore, during the process of performing separation using a specifically-binding substance, which specifically binds to specific lipid bilayer membrane particles or fragments thereof, for the purpose of increasing the efficiency of washing to efficiently remove unnecessary components without dropping the lipid bilayer membrane particles (fragments) binding to the solid phase, a solid phase having the form in which separation can be performed using a magnetic apparatus (a magnet) by introducing iron, a magnetic material, or the like into a particulate carrier may also be used. Such a solid phase that can be separated by a magnetic apparatus (a magnet) is generally known as a "magnetic bead".

In the detection method according to this aspect, in a case where the separation step to be described later is performed using the magnetic bead, the specifically-binding substance contains a magnetic bead or can bind to a magnetic bead. According to this, trapping of the specifically-binding substance in the separation step to be described later can be performed using a magnetic apparatus (a magnet). In a case where the specifically-binding substance contains a magnetic bead, the specifically-binding substance preferably binds to the magnetic bead. Further, in a case where the specifically-binding substance can bind to a magnetic bead, there are various embodiments of making the binding possible. For example, an embodiment in which the specifically-binding substance is labeled with one of biotin, avidin or a derivative thereof (for example, streptavidin, neutravidin, or the like) and then the magnetic bead is labeled with the other thereof is exemplified. Further, an embodiment in which the specifically-binding substance is labeled with glutathione-S-transferase (GST) (in a case where the specifically-binding substance is a protein, preferably, GST fusion protein is used as the specifically-binding substance) and the magnetic bead is labeled with glutathione is exemplified. Among these, an embodiment in which the specifically-binding substance is labeled with biotin and the magnetic bead is labeled with avidin or a derivative thereof, an embodiment in which the specifically-binding substance chemically binds directly to the magnetic bead, and the like are preferably employed.

Further, in the case of using a magnetic bead, the magnetic bead is preferably subjected to a blocking treatment. By performing the blocking treatment on the magnetic bead, it is possible to prevent foreign substances (a protein, lipid, sugar, and the like other than the measurement target substance), a dye staining a lipid bilayer membrane, or the like in the measurement sample from non-specifically adsorbing or binding to the magnetic bead, and thus substances other than the target lipid bilayer membrane particles or fragments thereof can be prevented from binding to the magnetic bead. As a result, emission of the dye in a case where the lipid bilayer membrane particles or fragments thereof do not exist is reduced and it is possible to detect desired lipid bilayer membrane particles or fragments thereof with higher accuracy.

The blocking treatment of the magnetic bead can be performed by bringing the magnetic bead into contact with a blocking agent. As described above, the magnetic bead may bind to the specifically-binding substance or can indirectly bind to the specifically-binding substance by being labeled with avidin (or a derivative thereof) or an anti-biotin antibody, but even in any cases, the blocking treatment may be performed before the specifically-binding substance, avidin (or a derivative thereof), or an anti-biotin antibody is allowed to bind to the magnetic bead or the blocking treatment may be performed after these are allowed to bind to the magnetic bead. There is no particular limitation on specific embodiments of the blocking agent to be used in the blocking treatment, and conventionally known knowledge may be appropriately referred to. Examples of the blocking agent include skim milk, fish gelatin, bovine serum albumin (BSA), a surfactant, casein, protamine, polyethylene glycol, trehalose, and dextran. Further, from the viewpoint that those which are formed from chemically synthesized substances other than a component derived from animals such as skim milk, fish gelatin, or bovine serum albumin (BSA) have stable characteristics and functions, commercially available blocking agents such as ECL Blocking Agent and ECL Prime Blocking Reagent (all manufactured by GE Healthcare Japan Corporation) are also preferably used. Only one of the blocking agents may be used or two or more thereof may be used in combination.

Incidentally, there is no particular limitation on the amount of the specifically-binding substance added to the biological sample, and the amount thereof can be appropriately determined with reference to conventionally well-known knowledge. Further, for example, in a case where an antibody or an engineered antibody is used as the specifically-binding substance, the antibody or the engineered antibody as the specifically-binding substance is added and then reacted with an antigen existing on the surfaces of the lipid bilayer membrane particles or fragments thereof contained in the biological sample (a surface antigen). At this time, the reaction condition for sufficiently promoting the antigen-antibody reaction between the antibody or the like and the surface antigen is not particularly limited, and conventionally well-known knowledge may be appropriately referred to. For example, it may be performed by incubation at room temperature for about 5 to 30 minutes. In addition, after completion of the reaction, the sample maybe diluted using a buffer solution (for example, phosphate buffered saline (PBS) or the like).

(Separation Step)

In this step, the specifically-binding substance added to the biological sample in the aforementioned specifically-binding substance addition step is trapped. Through this operation, it is possible to separate the lipid bilayer membrane particles or fragments thereof having predetermined molecules existing on surfaces to which the specifically-binding substance specifically binds.

In this step, a specific method of trapping the specifically-binding substance and separating predetermined lipid bilayer membrane particles or fragments thereof by the trapping of the specifically-binding substance is not particularly limited and may be appropriately selected depending on the form of the label (modification) which is applied to the specifically-binding substance and used for enabling the separation. For example, in a case where the specifically-binding substance contains a magnetic bead or can bind to a magnetic bead, the separation step can be performed by using a magnetic apparatus (a magnet). Further, a method for separating the lipid bilayer membrane particles or fragments thereof to which the specifically-binding substance binds by using a cell sorter is also exemplified. Incidentally, in the case of using the magnetic bead, Magnetic-Particles-DM and the like are exemplified as a commercially available product. The magnetic bead is preferably a complex of magnetic microparticles such as triiron tetraoxide and a polymer such as polystyrene, but is not limited thereto. In a case where the magnetic bead is a polymer complex, magnetic microparticles are dispersed in the magnetic bead to be embedded, and the magnetic microparticles exhibit superparamagnetic properties that they are magnetized near the magnet and magnetization is lost as they are away from the magnet. As a method for binding the specifically-binding substance to the magnetic bead, the magnetic bead is surface-treated and added with a functional group such as an amino group or a carboxyl group, and thus can chemically fix various substances or can be used as an ion exchanger. A person skilled in the art can appropriately use, for example, Dynabeads (R), Mag Sepharose, Therma-Max (R), Sepa-Max (R), and the like. In the case of indirect binding, it is particularly preferable that the magnetic bead be those to which avidin or a derivative thereof that simply and firmly binds to biotin, which is a low molecular, is immobilized, those in which the specifically-binding substance chemically binds directly to the magnetic bead, and the like.

Incidentally, in a case where information on the size of the lipid bilayer membrane particles serving as a measurement target is desired to be detected simultaneously, the particle size of the magnetic bead is preferably equal to or less than the minimum detection sensitivity of the measurement system. For example, in an existing general flow cytometer, the particle size of the magnetic bead is preferably 0.5 µm or less in the case of forward-scattered light (FS), and the particle size thereof is preferably 0.2 µm or less that is the minimum resolution in a general visible range image cytometer. In this case, since the area is divided by defining the size of the lipid bilayer membrane particles serving as a measurement target and then a count value can be obtained, the lipid bilayer membrane particles having a predetermined surface antigen and a predetermined size can be quantified. For example, by counting the number of events in which the forward-scattered light (FS) in the lipid staining measurement gate is 0.5 to 1.0 µm, the number, etc. of microparticles (MPs) defined by International Society on Thrombosis and Haemostasis (ISTH) or the like can be counted (quantified). This is very effective in a case where the measurement item that cannot be measured only to the research level in the related art is applied to the clinical test and the like.

Meanwhile, in a case where particles having a small size of submicron scale or less or fragments thereof are detected, if only the number of the particles and fragments is desired to be counted without obtaining information on size, the particle size of the magnetic bead can also be set within the detection area. According to this, by counting the number of events in which the forward-scattered light (FS) in the lipid staining measurement gate is integral multiple of the size of the magnetic bead, minute particles and fragments can be counted in the state in which the sensitivity is further improved. This is very effective in a case where minute substances such as exosomes are detected and the detected substances are applied to the clinical test and the like.

From the point of view as described above, the specific value of the particle size (diameter) of the magnetic bead can be appropriately set, but for example, the particle size (diameter) of the magnetic bead is preferably 50 to 3000 nm.

In this step, if the substance specifically binding to specific lipid bilayer membrane particles or fragments thereof (specifically-binding substance) binds directly to a solid phase (for example, a magnetic bead), the specific lipid bilayer membrane particles or fragments thereof as a target can be trapped directly in the solid phase. Alternatively, a specific cell as a target may be trapped indirectly in the solid phase by the solid phase to which a substance, which can recognize and trap the substance specifically binding to the specific lipid bilayer membrane particles or fragments thereof (specifically-binding substance), binds. It is desirable that the magnetic apparatus can separate lipid bilayer membrane particles or fragments thereof having magnetic beads, and as a commercially available apparatus, for example, MACS and Cell Separation Magnet are exemplified; however, the magnetic apparatus is not limited thereto, and any of magnetic apparatuses capable of separating specific lipid bilayer membrane particles or fragments thereof by using a magnetic bead and any of magnetic beads may be used.

The lipid bilayer membrane particles or fragments thereof serving as a detection target that are separated by using a solid phase such as a magnetic bead are subjected to a treatment such as washing as necessary, and then are provided to the detection step to be described later.

(Detection Step)

In this step, the lipid bilayer membrane particles or fragments thereof separated in the aforementioned separation step are detected on the basis of emission of the dye (the dye staining lipid) added in the dye addition step. Specific embodiments of the detection of the lipid bilayer membrane particles or fragments thereof on the basis of emission of the dye are not particularly limited. Although conventionally known knowledge typified by an embodiment using a fluorescent dye, an embodiment using a colored magnetic bead, or the like is appropriately referred to, the detection is preferably performed by flow cytometry or imaging cytometry. Specific procedures for performing detection by flow cytometry or imaging cytometry are not particularly limited, and conventionally known knowledge may also be appropriately referred to as long as a correct value can be accurately obtained.

In the detection method according to the present disclosure, a target stained by a dye is a lipid bilayer membrane itself. Therefore, the amount of the dye staining the lipid bilayer membrane particles or fragments thereof serving as a detection target is sufficiently large, and the detection does not depend on the amount of the predetermined molecules (for example, membrane proteins) existing on the surfaces of the lipid bilayer membrane particles or fragments thereof unlike the detection using a fluorescence-labeled antibody that is conventionally and generally used. For this reason, for example, when emission of the dye is measured by flow cytometry, the lipid bilayer membrane itself emits fluorescence, and thus sufficient fluorescence intensity can be ensured. As a result, the detection can be performed at a sufficient S/N ratio with respect to background autofluorescent light that may be a noise source. On the other hand, in the techniques of the related art, since the fluorescence intensity depends on the amount of the surface antigen (caused by a difference due to an amount of an identification marker distributed on the cell surface, largeness of surface area of microparticles, a difference between patients, or a difference due to disease states), there is a problem in that a target fluorescence intensity (that is, S/N ratio) cannot be sufficiently ensured.

By utilizing this point, it is preferable to measure fluorescence intensities of fluorescences of two or more colors having a different fluorescence wavelength by using a plurality of channels in the detection of the lipid bilayer membrane particles or fragments thereof. In a preferred embodiment, at least one of fluorescences of two or more colors having a different fluorescence wavelength is fluorescence emitted from the dye, and at least another one is autofluorescent light emitted from the lipid bilayer membrane particles or fragments thereof serving as a detection target.

In a preferred embodiment of this step, quantitative determination of the detected lipid bilayer membrane particles or fragments thereof can be performed. Herein, in a case where the detection target is particles closed by the lipid bilayer membrane (for example, extracellular vesicles), the particles are stained and emission of fluorescence or the like occurs in proportion to the surface area thereof. Therefore, for example, when fluorescence intensities of different wavelengths (for example, the fluorescence intensity of the fluorescence wavelength emitted from the dye and the fluorescence intensity of the fluorescence wavelength of the autofluorescent light) are plotted in the X axis and the Y axis of the two-dimensional plot diagram, respectively, the linear relation is maintained. Further, it can be determined that the events of the areas in this linear relation are the lipid bilayer membrane particles or fragments thereof serving as a detection target. Further, in a case where the scattered light intensity is plotted in one axis, the correlation according to the scattering theory (for example, cross-sectional area in the case of the Fraunhofer diffraction area) is maintained. For this reason, on the basis of scattered light intensity information obtained in this way, a distribution chart (histogram) based on the size of the detected lipid bilayer membrane particles or fragments thereof can be created. Then, the number of the lipid bilayer membrane particles or fragments thereof for each size defined in advance is measured so that the quantitative determination can be completed. Herein, for example, the size of the microparticles (MPs) is defined by International Society on Thrombosis and Haemostasis (ISTH), the lower limit of the size is set to 500 nm (0.5 μm) from the minimum sensitivity of the forward-scattered light of a flow cytometer that is an analyzing platform, and the upper limit of the size is set to 1000 nm (1.0 μm) for the purpose of excluding the influence of small-sized blood platelets or apoptotic bodies (ABs). Incidentally, in a case where the biological sample containing the detection target is subjected to filtering in advance through a pre-treatment step or the like, creation of the histogram based on the scattered light intensity information and the counting step based on this histogram are omitted, and the number of the measured particles or fragments thereof can be used in quantitative determination without any changes. Further, as described above, when the distribution chart (histogram) based on the size is created in a case where separation using a magnetic bead is performed, generally, it is necessary to set the size of the magnetic bead to be sufficiently smaller than the lower limit for defining the size of the detection target. However, depending on circumstances, even when the size of the magnetic bead is set to be sufficiently larger than the upper limit for defining the size of the detection target, counting (quantitative determination) can be performed (although the size cannot be identified).

Herein, in this step, an example of the specific method of performing quantitative determination of particles (fragments) in the microparticle (MP) areas in the detected lipid bilayer membrane particles or fragments thereof by flow cytometry will be described with reference to FIG. 1. Incidentally, hereinafter, the description will be given by using, as an example, a case where a fluorescent dye to be used in lipid staining has a first fluorescence wavelength (FL1) and has a second fluorescence wavelength (FL2).

The "first plot" as shown in FIG. 1 is a two-dimensional plot using forward-scattered light (FS; Forward Scatter) and side-scattered light (SS; Side Scatter) (for example, X axis=FS(Log), Y axis=SS(Log)). According to this, it is possible to obtain information on the size of measurement target particles using the scattered light.

Subsequently, in order to adjust the sensitivity setting of the flow cytometer, 1 μm standard particle size beads (made of polystyrene or the like) are measured. Then, a histogram of particle events serving as a measurement target (a seventh plot to be described later: X axis=FS(Log), Y axis=the number of events) is created, and FS sensitivity is adjusted such that the peak position of the event becomes, for example, the X-axis address of $10^1$. Meanwhile, regarding SS sensitivity, sensitivity is adjusted such that the entire events are included. Incidentally, in a case where the lipid bilayer membrane particles and the like serving as a measurement target are smaller than the minimum detection sensitivity of FS of the flow cytometer (a submicron area in a general flow cytometer), it is preferable to use SS as the index of the size instead of FS. In this case, an SS histogram is created by measuring fine standard particle size beads, the SS sensitivity is adjusted such that the peak position of the event becomes, for example, the X-axis address of $10^1$, and regarding the FS sensitivity, the sensitivity may be adjusted such that the entire events are included.

Next, the "second plot" is a two-dimensional plot using a fluorescence intensity (FL1) of a first fluorescence wavelength (for example, 525 nm) and a fluorescence intensity (FL2) of a second fluorescence wavelength (for example, 575 nm) (for example, X axis=FL2(Log), Y axis=FL1(Log)). According to this, it is possible to simultaneously obtain information on the fluorescence wavelengths of two colors by lipid staining of the measurement target particles and to set a gate (EV gate) for separating the measurement target particles from an autofluorescent light substance.

Figure 2B:
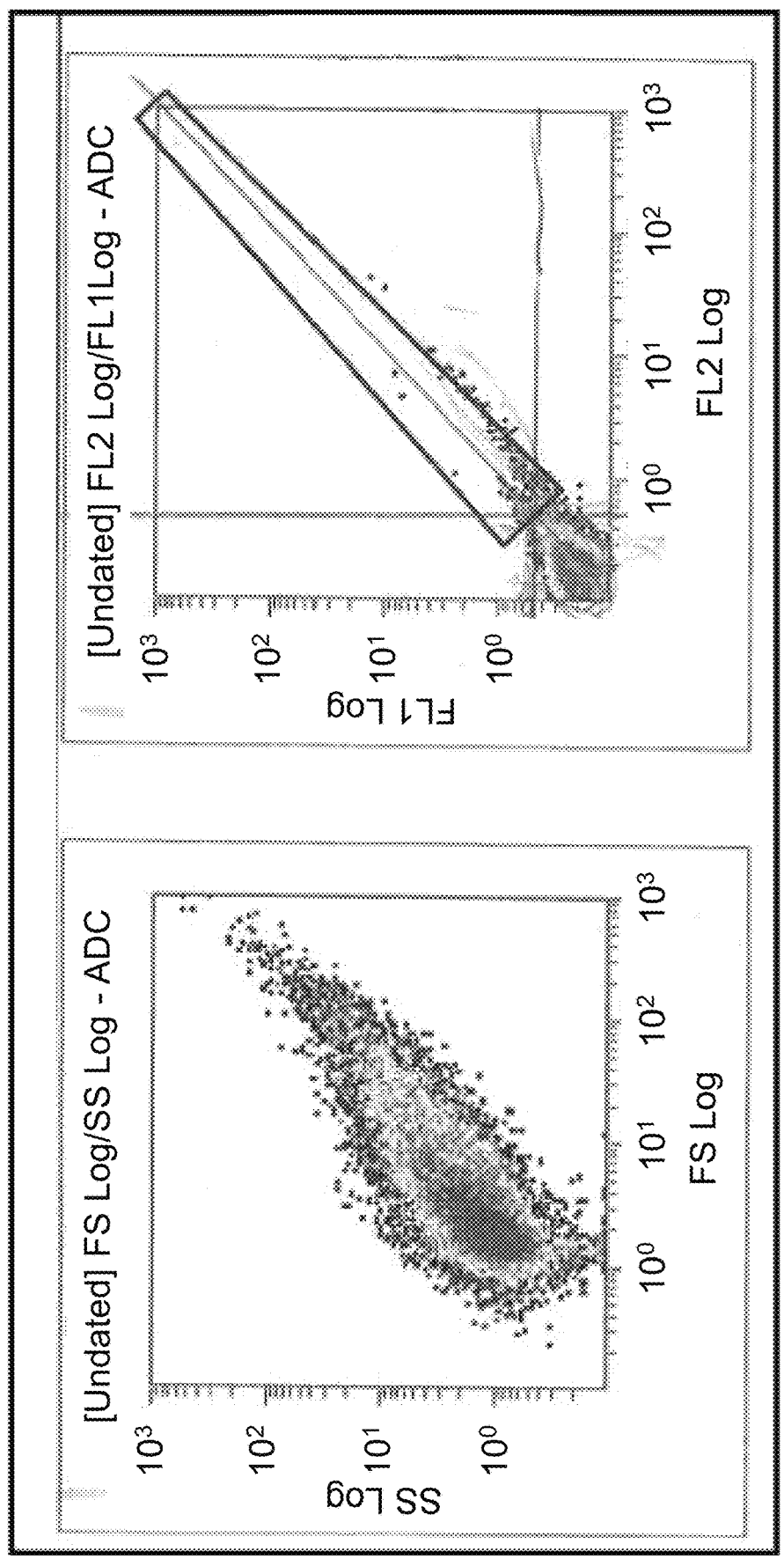
FIG. 2B shows the measurement results of the same vesicles not subjected to lipid staining.
Figure 3A:
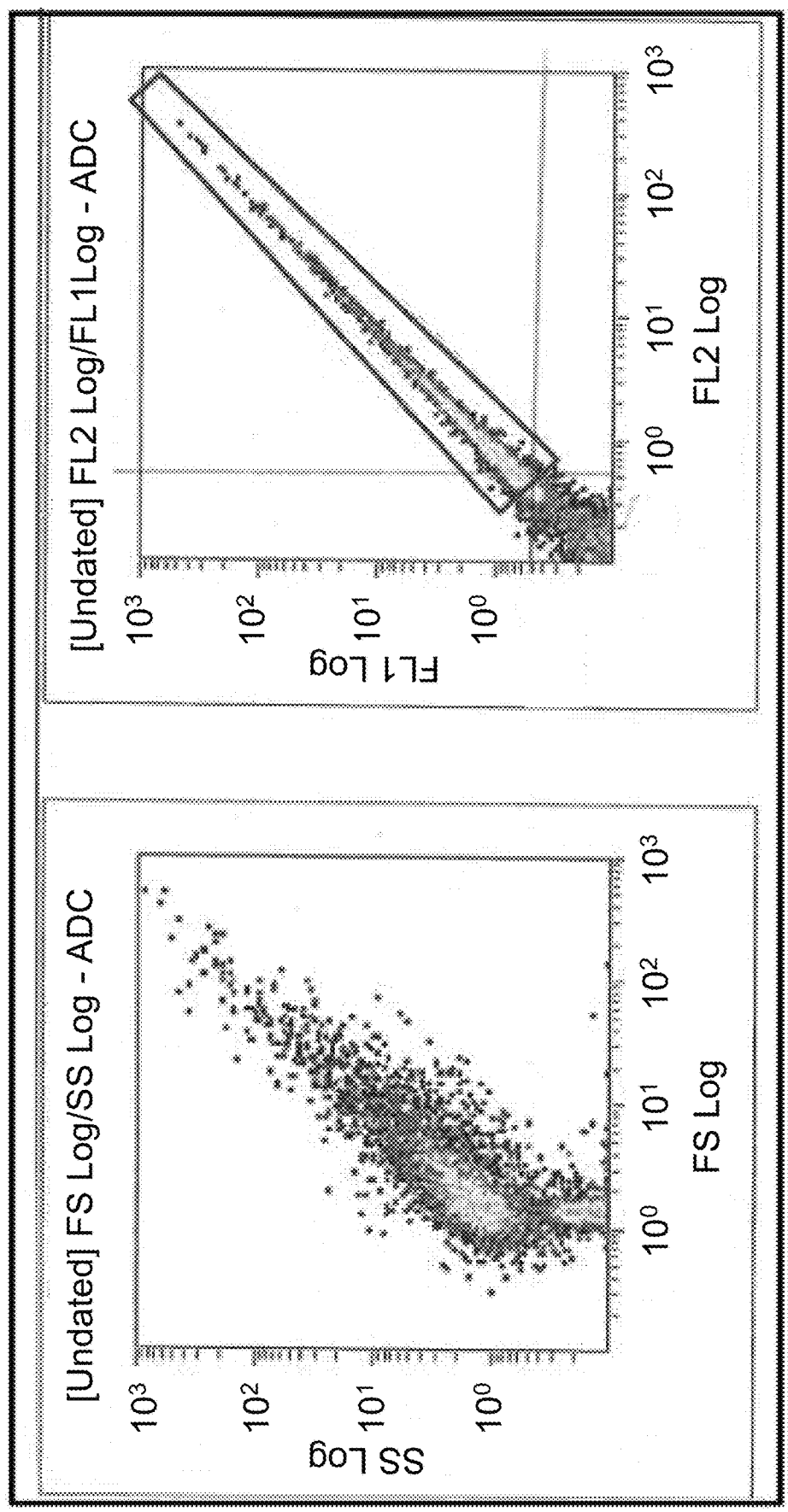
FIGS. 3A and 3B are diagrams showing the flow cytometry measurement results of fetal bovine serum (FBS)
Figure 3B:
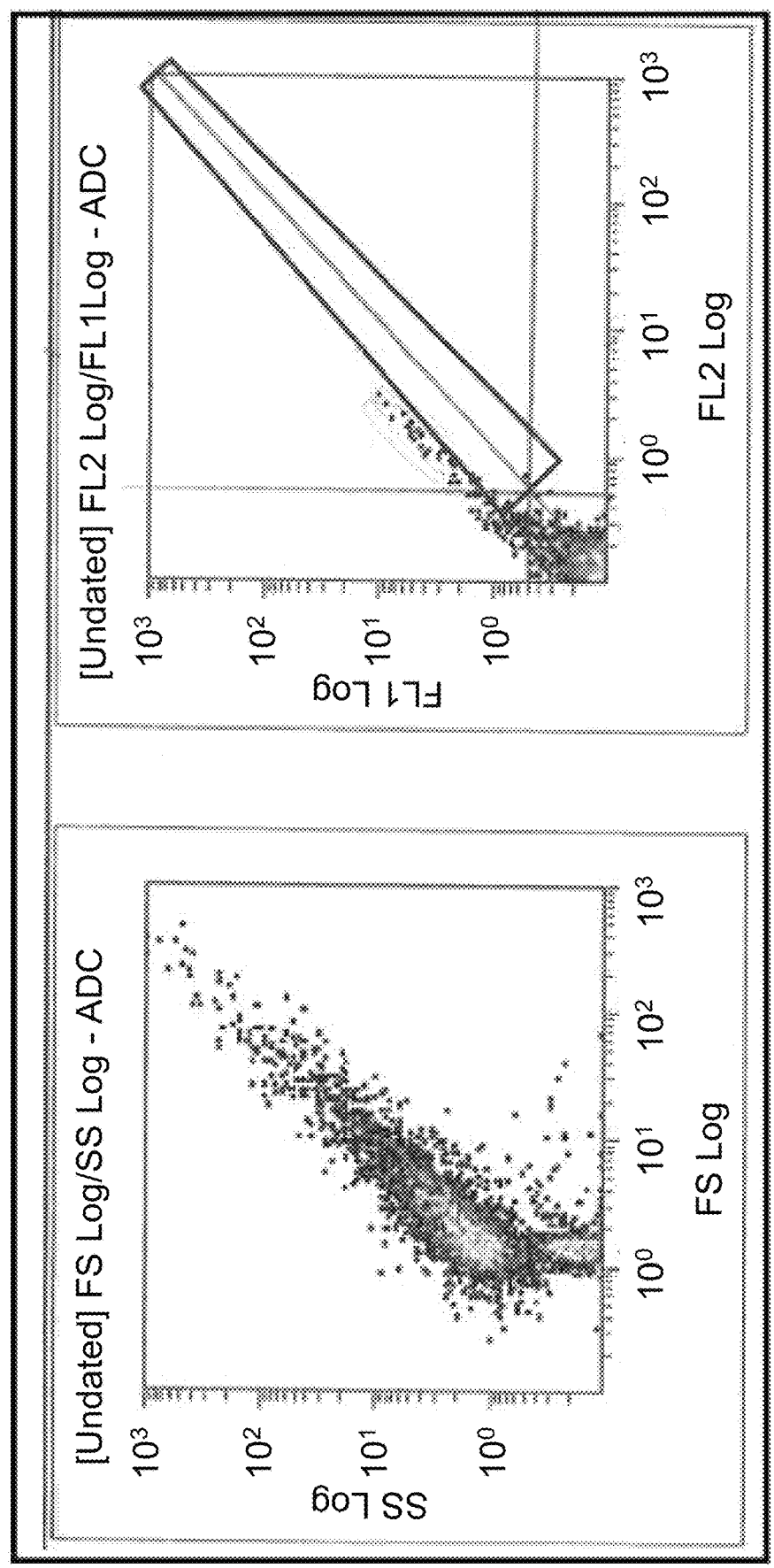
Figure 4A:
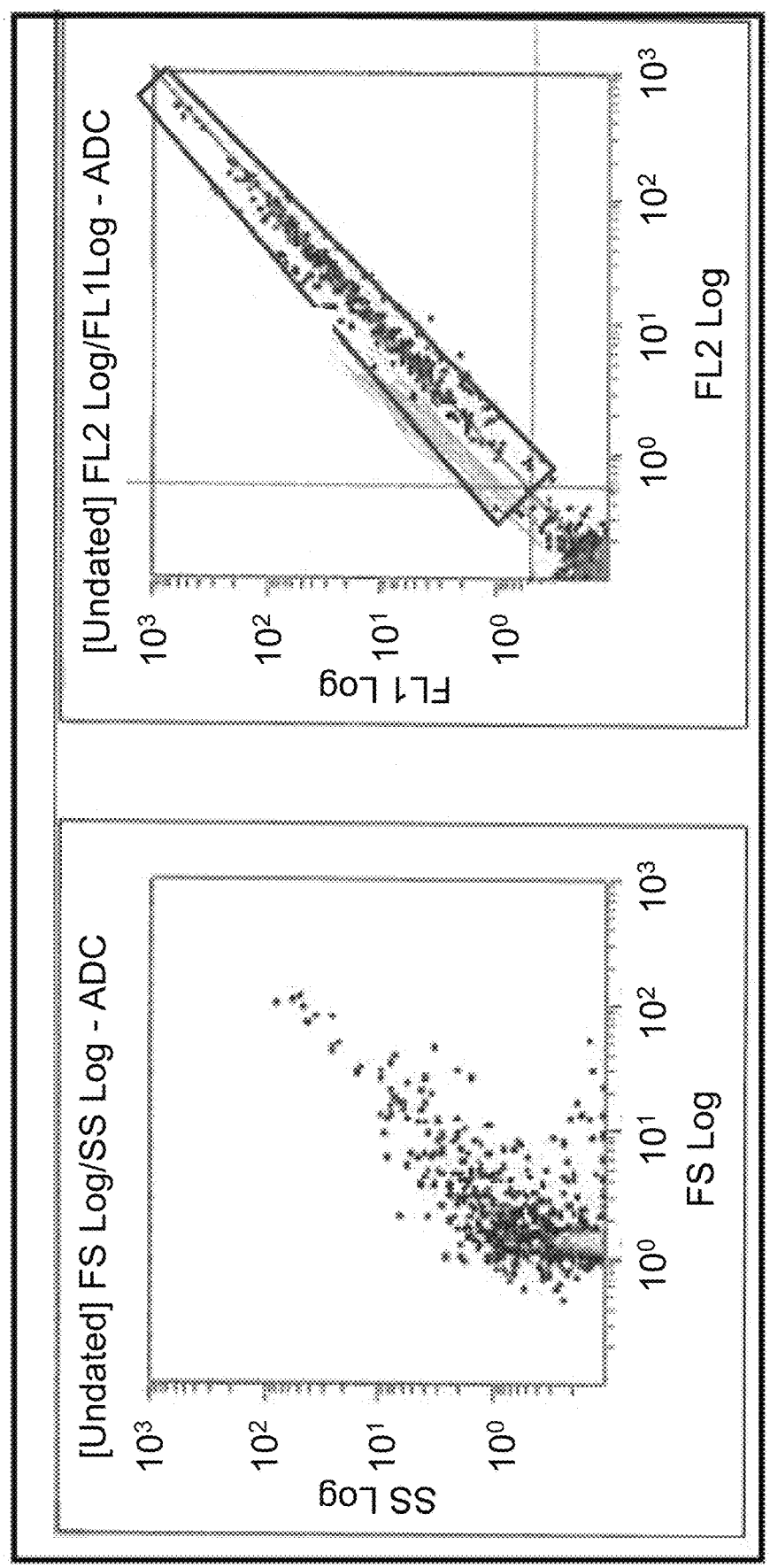
FIGS. 4A and 4B are diagrams showing the flow cytometry measurement results of OVCAR-3 cells.
Figure 4B:
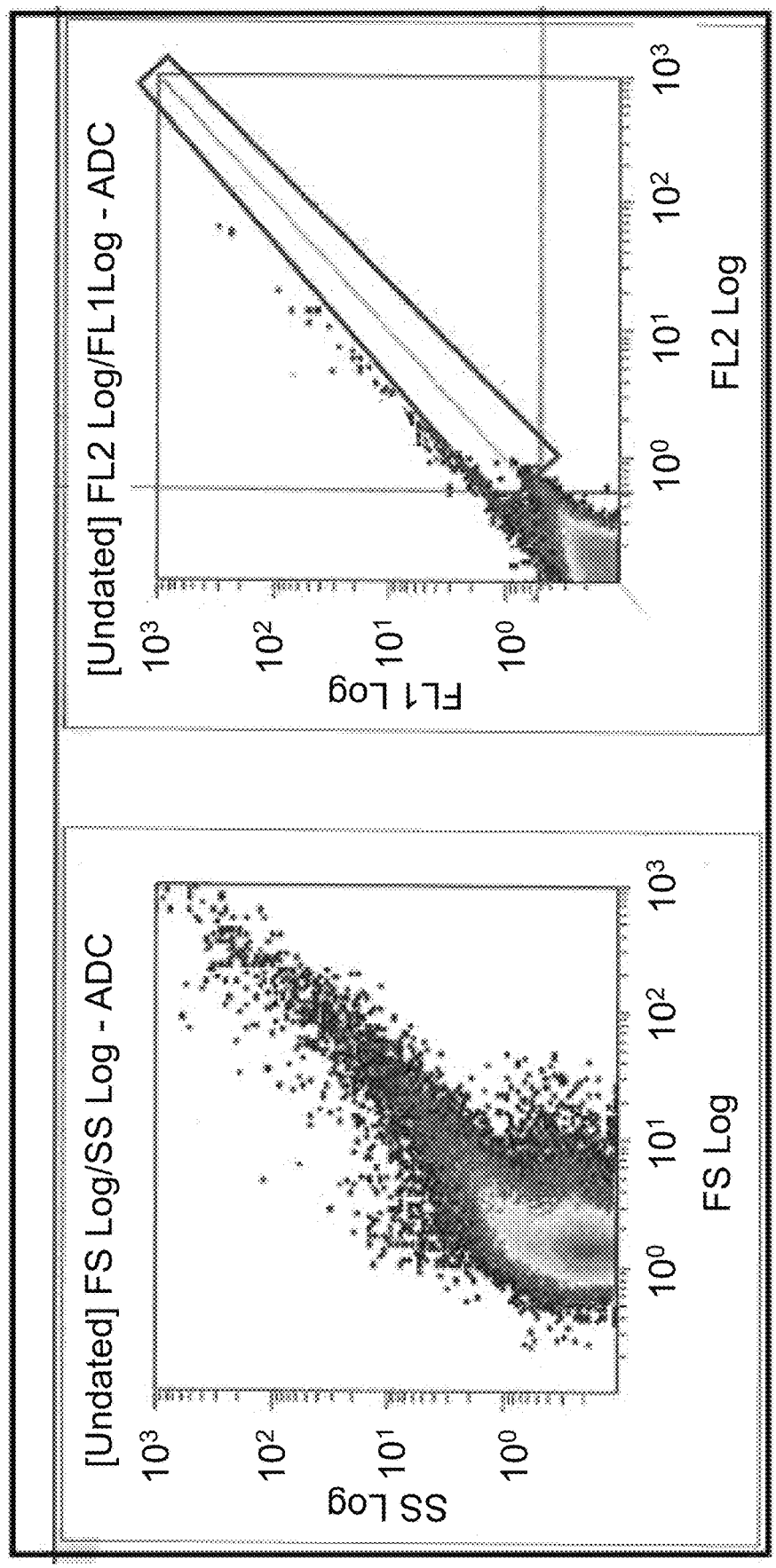

Subsequently, in order to adjust the sensitivity setting of the flow cytometer, the lipid bilayer membrane particles and the like are measured. Then, sensitivity is adjusted such that the lipid staining event serving as a measurement target is y=[inclination]x+[intercept] (herein, [inclination]=1.0 and [intercept]=0.0) on the second plot. At this time, as the measurement target, lipid vesicles and the like in which there is almost no autofluorescent light in a staining sample maybe used. Herein, a first plot and a second plot obtained by measuring artificial lipid bilayer membrane vesicles (artificial liposome, DMPC: dimyristoylphosphatidylcholine) by flow cytometry are shown in FIGS. 2A and 2B. The FIG. 2A represents measurement results of the sample subjected to lipid staining by the method of the present disclosure, and the FIG. 2B represents measurement results of the sample not subjected to lipid staining. Similarly, a first plot and a second plot obtained by measuring fetal bovine serum (FBS) by flow cytometry are shown in FIGS. 3A and 3B (FIG. 3A: lipid-stained sample, FIG. 3B: lipid-non-stained sample), and a first plot and a second plot obtained by measuring OVCAR-3 cell by flow cytometry are shown in FIGS. 4A and 4B (FIG. 4A: lipid-stained sample, FIG. 4B: lipid-non-stained sample). Incidentally, in all samples in which the results shown in FIGS. 2A to 4B are measured, the EpCAM (CD326) antigen exists on the surfaces of the lipid bilayer membrane particles. Therefore, these results are obtained by using a fluorescence-labeled antibody (anti-CD326 antibody) with respect to the antigen and a fluorescent dye staining a lipid bilayer membrane. After the sensitivity on the second plot is adjusted in this way, a histogram of particle events serving as a measurement target (a fifth plot and a sixth plot to be described later: X axis=FL1(Log) or FL2(Log), Y axis=the number of events) is created, and the sensitivity of FL1 and FL2 is adjusted such that the upper limit position of the negative event becomes the X-axis address of $4 \times 10^0$ or less. At this time, the lower limit position of the EV gate of the second plot is set to be the X-axis address and the Y-axis address of $4 \times 10^0$.

The "third plot" is a two-dimensional plot using forward-scattered light (FS) and the fluorescence intensity (FL1) of the first fluorescence wavelength (for example, 525 nm) (X axis=FS(Log), Y axis=FL1(Log)). According to this, it is possible to simultaneously confirm information on the size of the lipid bilayer membrane particles serving as a measurement target and information on lipid staining. Incidentally, as necessary, a plot graph showing only the event of the second plot in the EV gate may be created.

The "fourth plot" is a two-dimensional plot, which is created in a similar manner to the "third plot", using the forward-scattered light (FS) and the fluorescence intensity of the second fluorescence wavelength (for example, 575 nm) (X axis=FS(Log), Y axis=FL1(Log)). According to this, it is possible to simultaneously confirm information on the size of the lipid bilayer membrane particles serving as a measurement target and information on lipid staining. Incidentally, also regarding the fourth plot, a plot graph showing only the event of the second plot in the EV gate may be created as necessary.

The "fifth plot" is a histogram of the fluorescence intensity (FL1) of the first fluorescence wavelength (for example, 525 nm) (X axis=FL1(Log), Y axis=the number of events). According to this, it is possible to confirm whether or not the lower limit position of the EV gate is appropriate from a difference in fluorescence intensity between the lipid staining event (positive event) of the lipid bilayer membrane particles serving as a measurement target and lipid non-staining event (negative event). Incidentally, as necessary, a plot graph showing only the event of the second plot in the EV gate may be created.

The "sixth plot" is a histogram of the fluorescence intensity (FL2) of the second fluorescence wavelength (for example, 575 nm), which is created in a similar manner to the "fifth plot" (X axis=FL2(Log), Y axis=the number of events). According to this, similarly to the above description, it is possible to confirm whether or not the lower limit position of the EV gate is appropriate from a difference in fluorescence intensity between the lipid staining event (positive event) of the lipid bilayer membrane particles serving as a measurement target and lipid non-staining event (negative event). Incidentally, also as for the sixth plot, as necessary, a plot graph showing only the event of the second plot in the EV gate may be created.

Finally, the "seventh plot" is a histogram of the forward-scattered light (FS) of the event of the third plot in the EV gate (X axis=FS(Log), Y axis=the number of events). According to this, the lipid bilayer membrane particles serving as a measurement target can be classified on the basis of information on size thereof and the count value of each group can be calculated (quantified). For example, the seventh plot (FS histogram) showing the entire measured EV (EV-all) is divided into three parts by using two types of standard beads (particle size of 0.5 μm and particle size of 1.0 μm) that are the definition of FS section microparticles (MPs). Further, regarding four items of EV-all, small EV (EV smaller than the MP area), MP (EV of the MP area), and large EV (EV larger than the MP area), a calculation value (the number of the lipid bilayer membrane particles) can be obtained. In this way, the quantitative determination of the lipid bilayer membrane particles having a predetermined surface antigen and a predetermined size is completed. Incidentally, also in the seventh plot, as necessary, a plot graph showing only the event of the second plot in the EV gate may be created (third plot: EV gate).

Further, when the lipid bilayer membrane particles serving as a measurement target are classified on the basis of information on size thereof and the count value of each group is calculated (quantified), the lipid staining amount can also be used instead of the forward-scattered light as the size information. In this case, the fifth plot or the sixth plot is used as an index of size, and the quantitative value according to the divided area of the histogram is calculated similarly to the seventh plot so that the calculation value (the number of the lipid bilayer membrane particles) based on arbitrary size information can be obtained.

Hereinbefore, the detection method of the present disclosure has been described by using the case of detecting (quantifying) the lipid bilayer membrane particles or fragments thereof in the biological sample by flow cytometry as an example, but depending on circumstances, detection (quantitative determination) may also be performed by another method. As a method which may be used in detection other than the flow cytometry, imaging cytometry or the like is exemplified.

According to a second aspect of the present disclosure, there is provided a detection kit for lipid bilayer membrane particles or fragments thereof, which is used in the aforementioned first aspect. The detection kit includes, as essential components, a dye staining a lipid bilayer membrane in a biological sample, a substance specifically binding to predetermined molecules existing on surfaces of the lipid bilayer membrane particles or fragments thereof (specifically-binding substance), and a separating reagent for trapping the substance and separating the lipid bilayer membrane particles or fragments thereof. Herein, since specific embodiments of the dye and the specifically-binding substance areas described above, detailed description is omitted here. Further, in a case where the specifically-binding substance contains a magnetic bead, the magnetic bead is used as the separating reagent. Therefore, in this case, the specifically-binding substance and the separating reagent are contained in the detection kit in the state of forming a complex. On the other hand, in a case where the specifically-binding substance can bind to a magnetic bead, the magnetic bead is contained in the detection kit separately from the specifically-binding substance.

Incidentally, in a case where detection is performed by using flow cytometry, the detection kit may further include setting beads for defining an upper limit and/or a lower limit of the size of lipid bilayer membrane particles or fragments thereof serving as a detection target, beads for calculation with known concentration, threshold beads for defining a threshold value of the minimum intensity in the detection area of the lipid bilayer membrane particles or fragments thereof, and the like. It is preferable to appropriately determine the average particle size of the threshold beads, the average particle size of the beads for calculation, and the average particle size of the setting beads by the aforementioned method with reference to FIG. 1 and the like.

The detection kit to be provided by the present disclosure may include, besides the aforementioned components, for example, a buffer solution for diluting a reagent and a sample, a reaction vessel, positive control, negative control, and written directive indicating test protocol, and the like. These elements can also be mixed in advance as necessary. By using this kit, the detection of the lipid bilayer membrane particles or fragments thereof in the present disclosure becomes simple, and is very useful for early decision on the course of treatment, diagnosis of prognosis, confirmation of treatment effect, and the like.

EXAMPLES

Hereinafter, the embodiments of the present disclosure will be described in more detail by means of Examples; however, the scope of the present disclosure is not intended to be limited to the following Examples.

(Comparative Example)

Figure 5A:
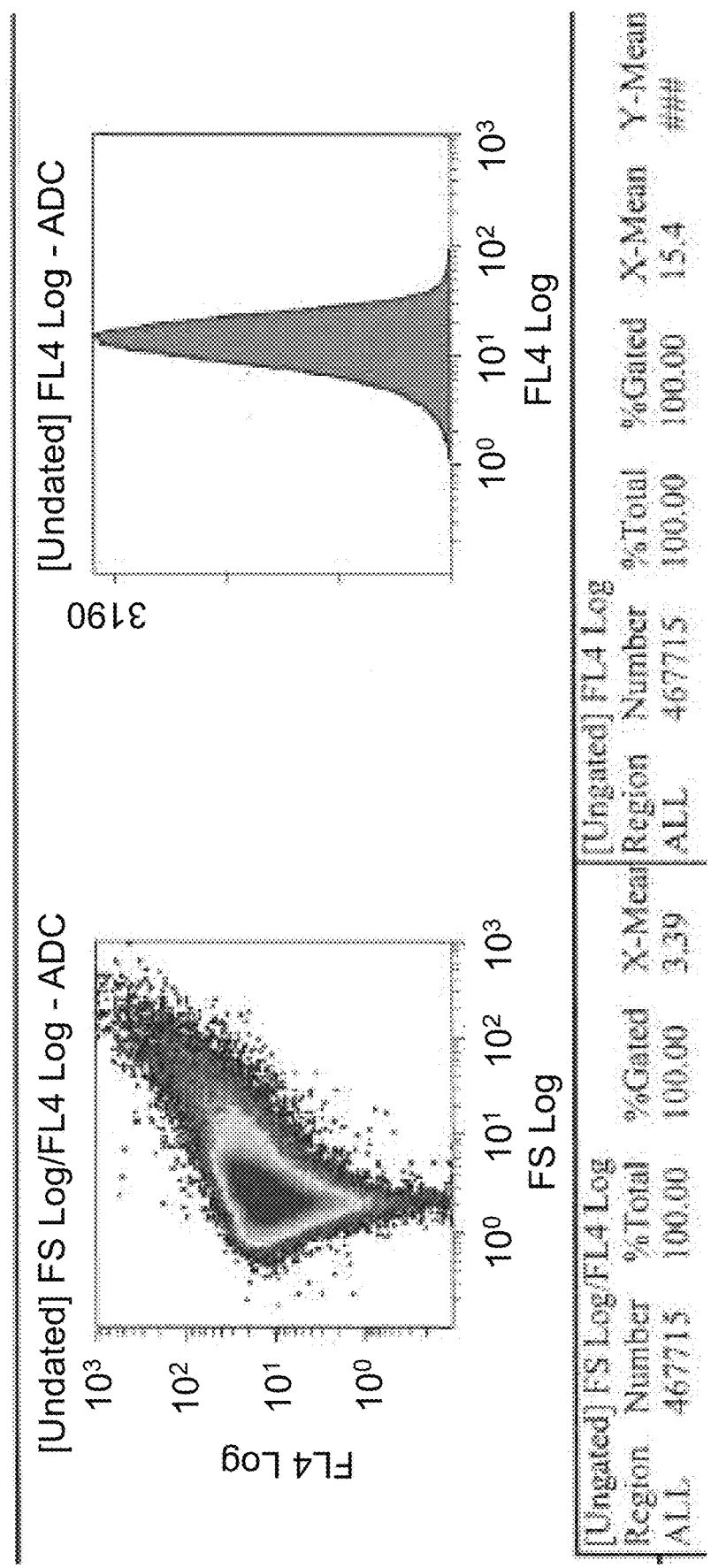
FIGS. 5A and 5B are histograms from a comparative example showing flow cytometry results obtained by detecting extracellular vesicles (EVs) released from A431 cells (a CD326 antigen exists on the surface) derived from human epidermoid cancer.

Detection of extracellular vesicles released from A431 cells (a CD326 antigen exists on the surface) derived from human epidermoid cancer was tried to be conducted by using a conventional technique. Specifically, the culture of the A431 cells was separated by centrifugation to remove large particles, the supernatant containing the extracellular vesicles was taken out, and then FBS was added thereto. Further, an anti-CD326 antibody labeled with fluorescent dye HiLyte (trademark) Fluor 647 was added, and the histogram of the fluorescence intensity (wavelength of 575 nm) obtained by performing measurement using flow cytometry is shown in FIG. 5A. Meanwhile, negative control in which the anti-CD326 antibody was not added is shown in FIG. 5B and the fluorescence intensity is distributed at the lower place as compared to the FIG. 5A.

Figure 5B:
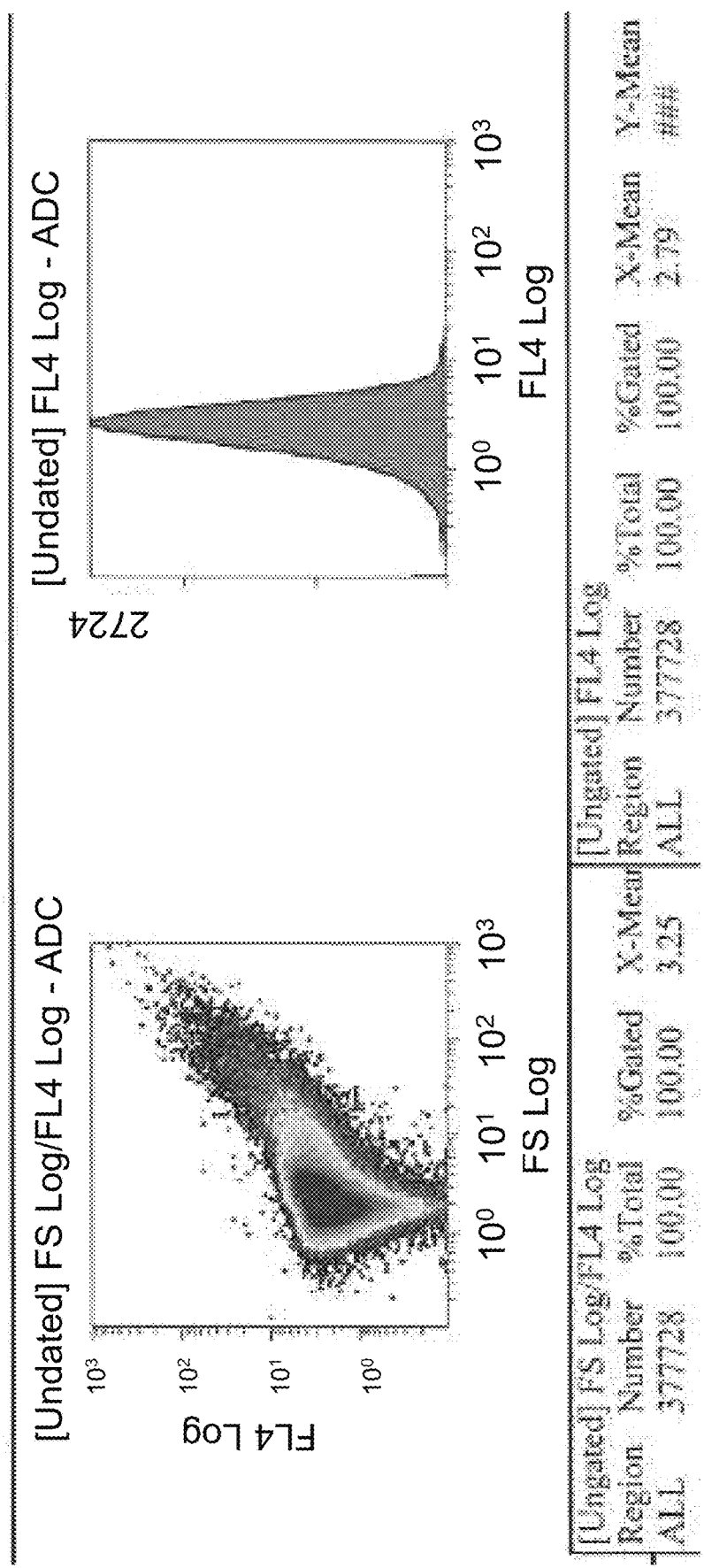

From the results presented in FIGS. 5A and 5B, it was found that the fluorescence intensity was increased by binding a fluorescence-labeled antibody to extracellular vesicles derived from A431 cells. However, it was found that there was a group that could not be separated from background fluorescence among fluorescences derived from the fluorescence-labeled anti-CD326 antibody since the upper stage histogram and the lower stage histogram overlapped to each other.

Example 1

Figure 6A:
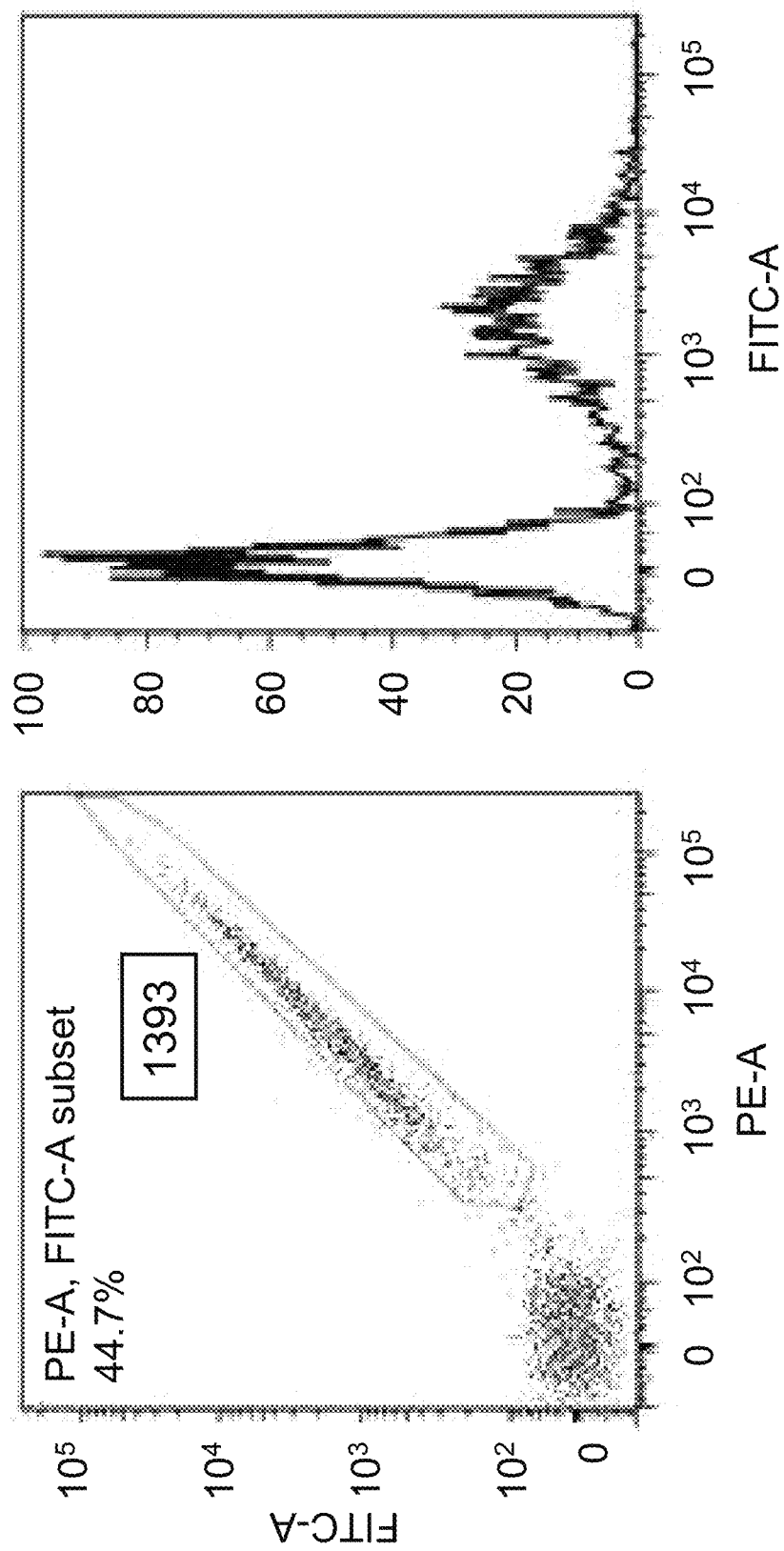
FIGS. 6A and 6B are diagrams showing a second plot and a sixth plot (histogram of fluorescence intensity at 525 nm) obtained by measuring extracellular vesicles released from A431 cells (a CD326 antigen exists on the surface) derived from human epidermoid cancer by flow cytometry.
Figure 6B:
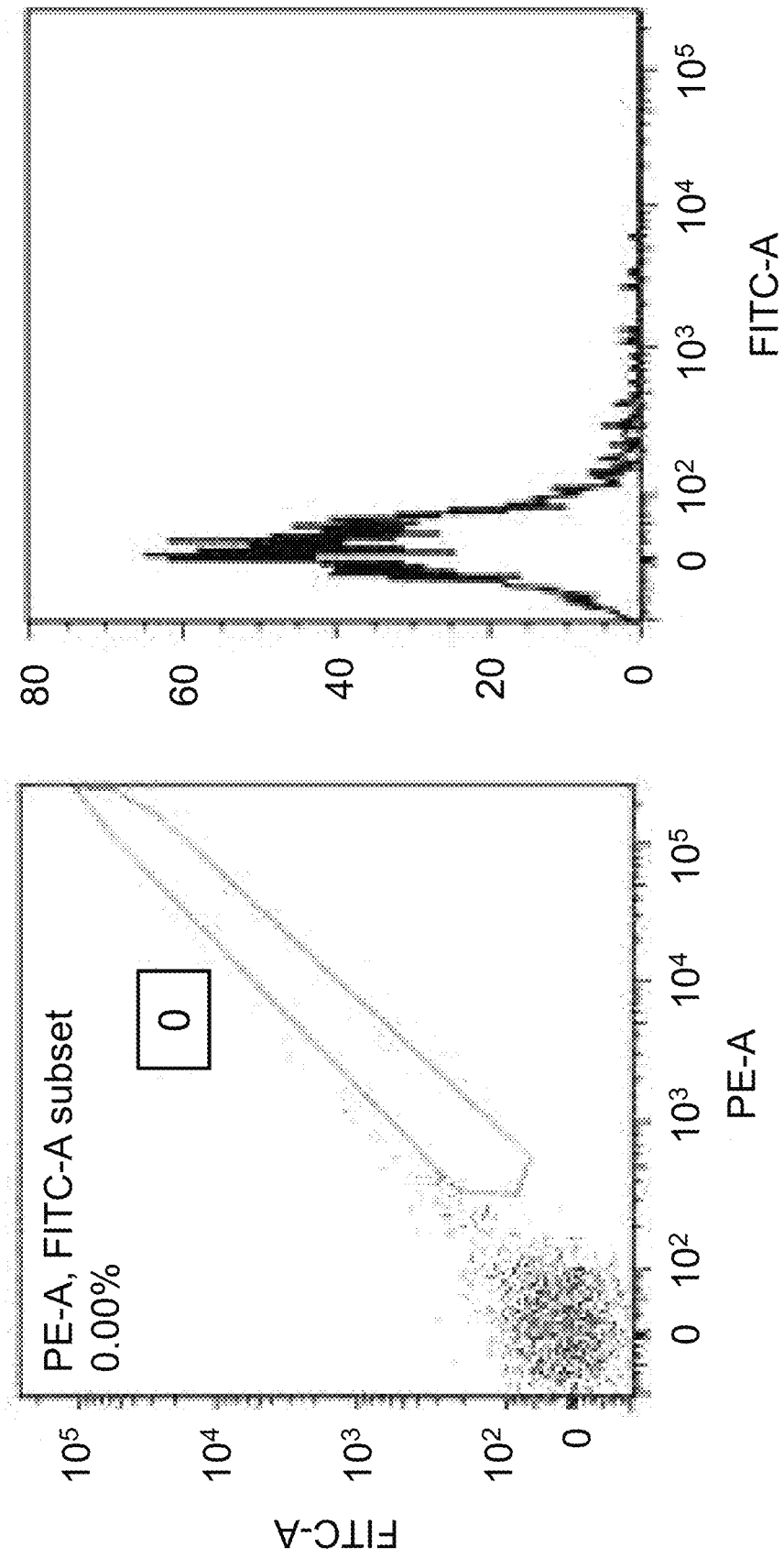

Similarly to the Comparative Example described above, detection of extracellular vesicles released from A431 cells (a CD326 antigen exists on the surface) derived from human epidermoid cancer was tried to be conducted. However, the detection method according to the present disclosure was applied to the detection. Specifically, the culture of the A431 cells was separated by centrifugation to remove large particles, the supernatant containing the extracellular vesicles was taken out, and then FBS was added thereto. Further, Polaric manufactured by GORYO Chemical, Inc. that is a dye staining lipid was added to this sample. Then, an anti-CD326 antibody with a magnetic bead (anti-CD326 magnetic bead manufactured by Miltenyi Biotec) was added thereto. Thereafter, the magnetic bead was trapped by using a magnet, and after washing, the magnet was removed and the solution was recovered. The recovered solution was provided to detection by using flow cytometry. At this time, the dye was excited by using a blue laser light source of 488 nm. The second plot and the sixth plot thus obtained (histogram of the fluorescence intensity (wavelength of 525 nm)) are shown in FIGS. 6A and 6B. Incidentally, the FIG. 6A represents measurement results of positive control, and the FIG. 6B represents measurement results of negative control.

From the results presented in FIGS. 6A and 6B, it was found that the fluorescent spectrum derived from the detection target could be obtained according to this Example separately from the fluorescent spectrum of the background fluorescence derived from the autofluorescent light. For this reason, the detection of the lipid bilayer membrane particles or fragments thereof serving as a detection target can be performed in the form of excluding the influence of the background fluorescence, that is, at a high S/N ratio. Further, at the time of the detection using flow cytometry in this Example, fluorescence intensities of fluorescences of two colors having a different fluorescence wavelength were measured by using two channels (the first fluorescence wavelength of 525 nm and the second fluorescence wavelength of 575 nm). The scattergram thus obtained (abscissa axis: fluorescence wavelength of 575 nm, ordinate axis: fluorescence wavelength of 525 nm) is shown in FIG. 7.

Figure 7:
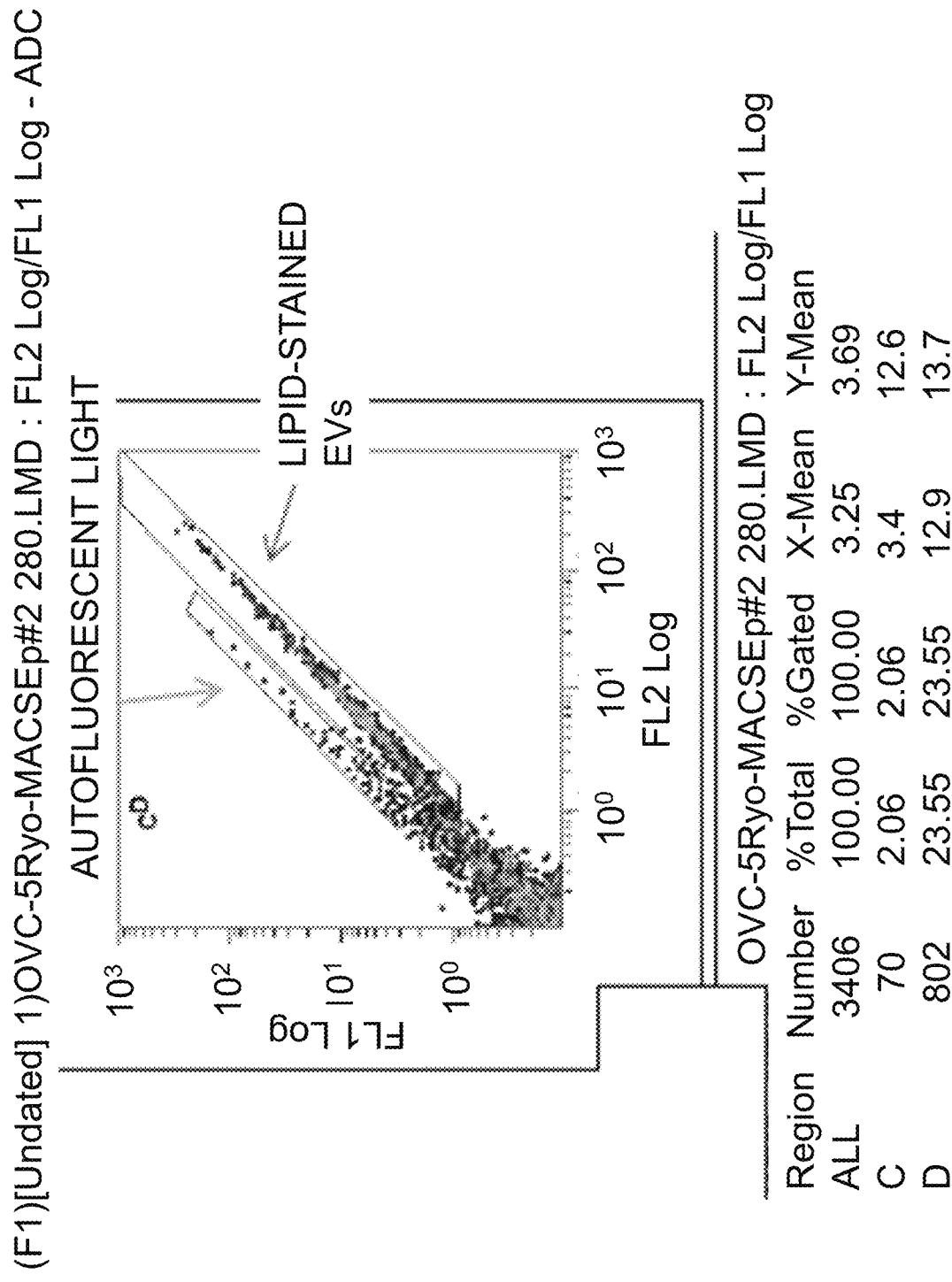
FIG. 7 is a scattergram obtained by measuring fluorescence intensities of fluorescences of two colors having a different fluorescence wavelength using two channels at the time of detection using flow cytometry in the Example to be described later.

As shown in FIG. 7, by appropriately selecting a plurality of fluorescence wavelengths at which the fluorescent spectrum of the dye staining lipid and the fluorescent spectrum of the autofluorescent light (background fluorescence) are different from each other, a ratio between wavelengths in the fluorescence intensity derived from the dye staining lipid can be differentiated from a ratio between wavelengths in the fluorescence intensity derived from the autofluorescent light, and complete separation on the scattergram can be performed. As a result, only the lipid bilayer membrane particles or fragments thereof serving as a detection target can be selectively detected with absolute accuracy.

Example 2

Subsequently, three types of parent cells having a different expression amount of the EpCAM (CD326) antigen on the cell surfaces were prepared, and a difference in the expression amount of the antigen on the surfaces of the respective cells was confirmed. Herein, as the parent cells, human ovarian serous adenocarcinoma-derived cell (OVCAR-3), human squamous cancer-derived cell (A431), and human prostate cancer-derived cell (PC3) were used. Incidentally, these cells were obtained from American Type Culture Collection (ATCC). Further, the expression amount of the EpCAM (CD326) antigen in respective cell surfaces of these parent cells is known to be PC3<A431<OVCAR-3. For this reason, the detection of the lipid bilayer membrane particles (extracellular vesicles) was tried to be performed by confirming the surface antigen amount in these parent cells, then causing the lipid bilayer membrane particles (extracellular vesicles) to be expressed from these parent cells, and carrying out the detection method according to the present disclosure. According to this, it was tested whether or not the detection can be performed by the detection method according to the present disclosure regardless of the amount of the surface antigen.

Specifically, first, the amount of the antigen on the surfaces of the three types of parent cells prepared above was confirmed by using a flow cytometer.

At this time, in the detection of positive control, an anti-EpCAM mouse antibody was used as a primary antibody and an anti-mouse IgG antibody labeled with a phycoerythrin (PE) fluorescent dye was used as a secondary antibody. Meanwhile, in the detection of negative control, only an anti-mouse IgG antibody labeled with a PE fluorescent dye was used as a secondary antibody without using a primary antibody.

Figure 8A:
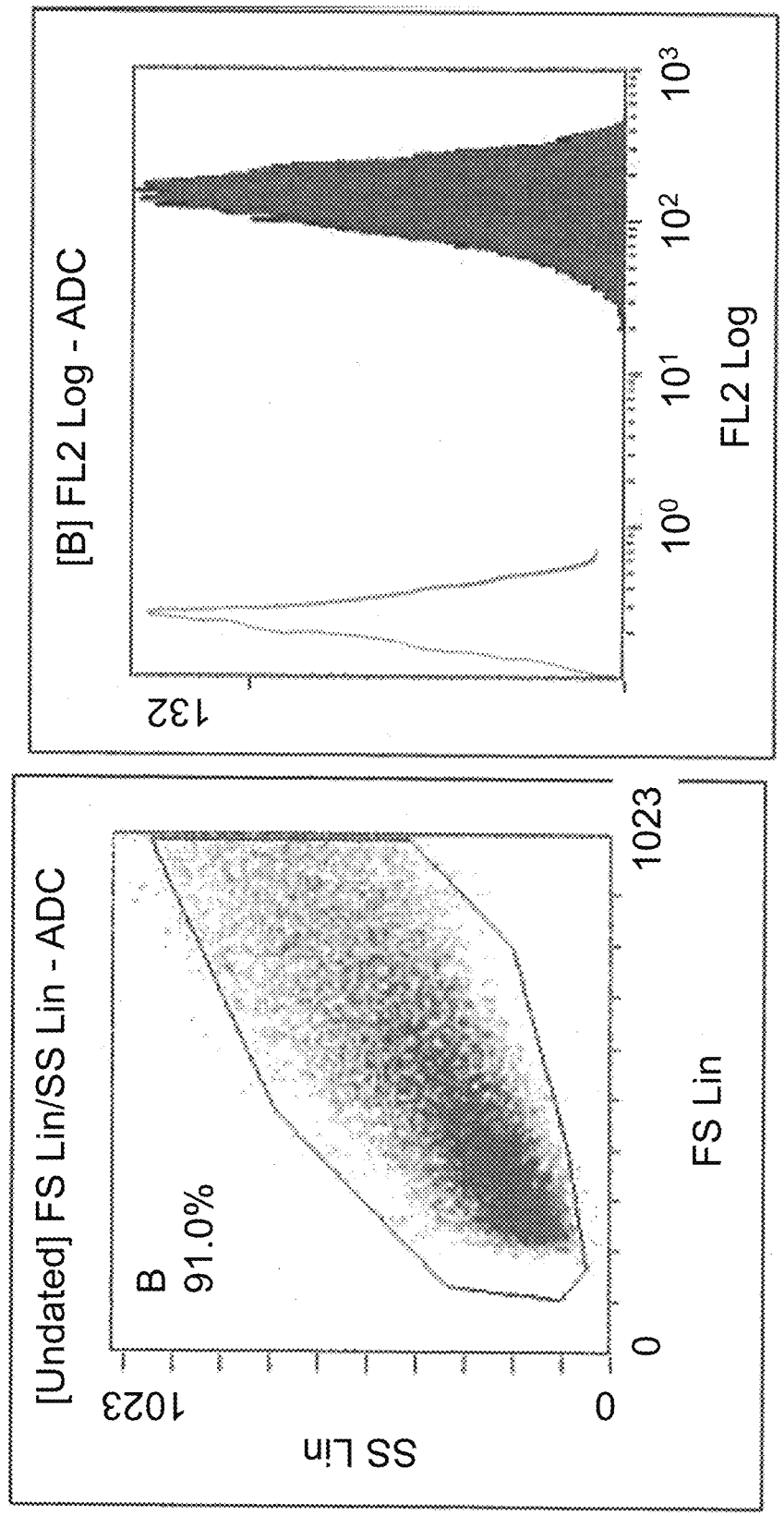
FIGS. 8A and 8B are diagrams showing a first plot and a sixth plot obtained by measuring OVCAR-3 cells by flow cytometry.
Figure 8B:
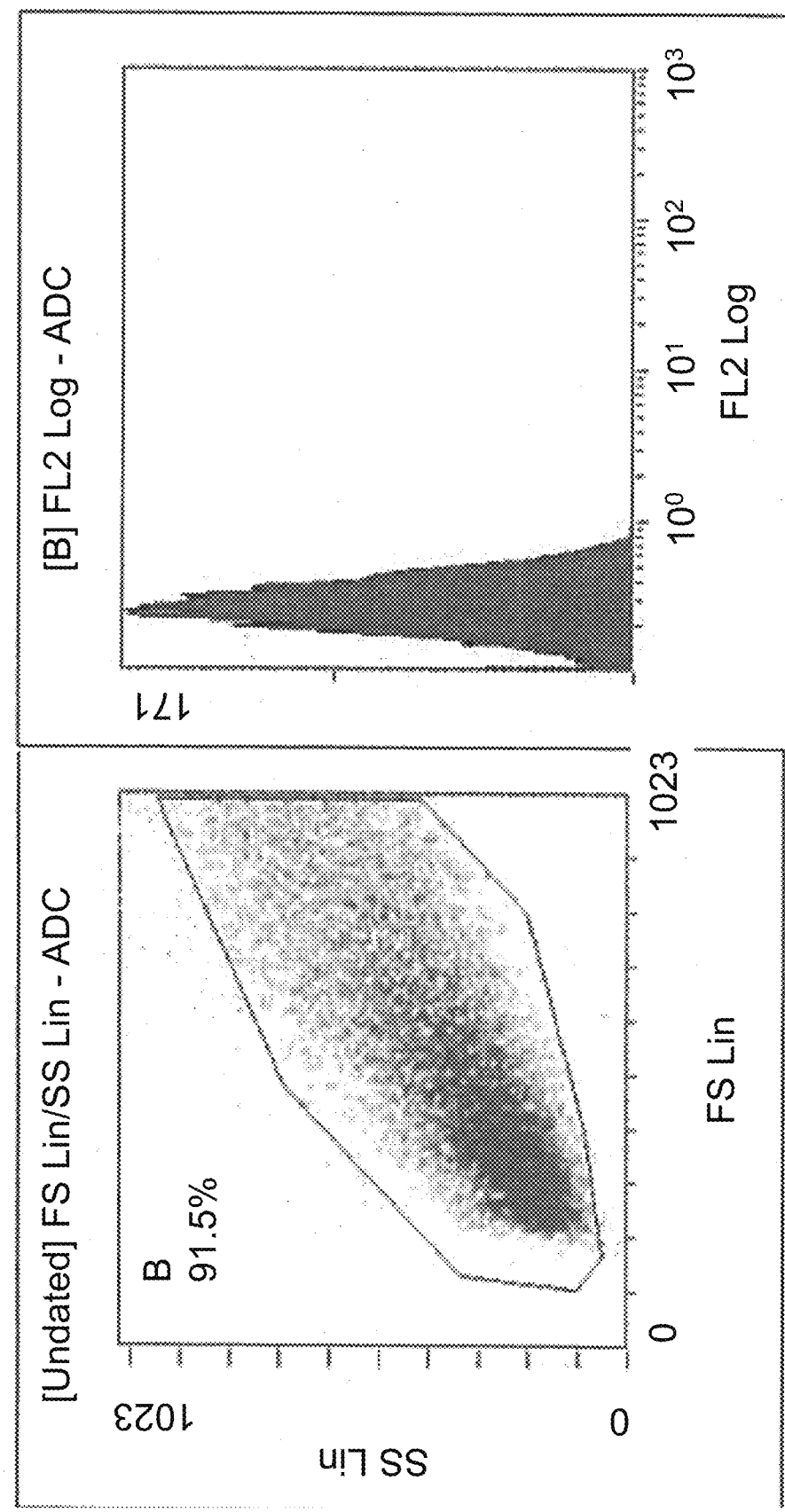
Figure 9B:
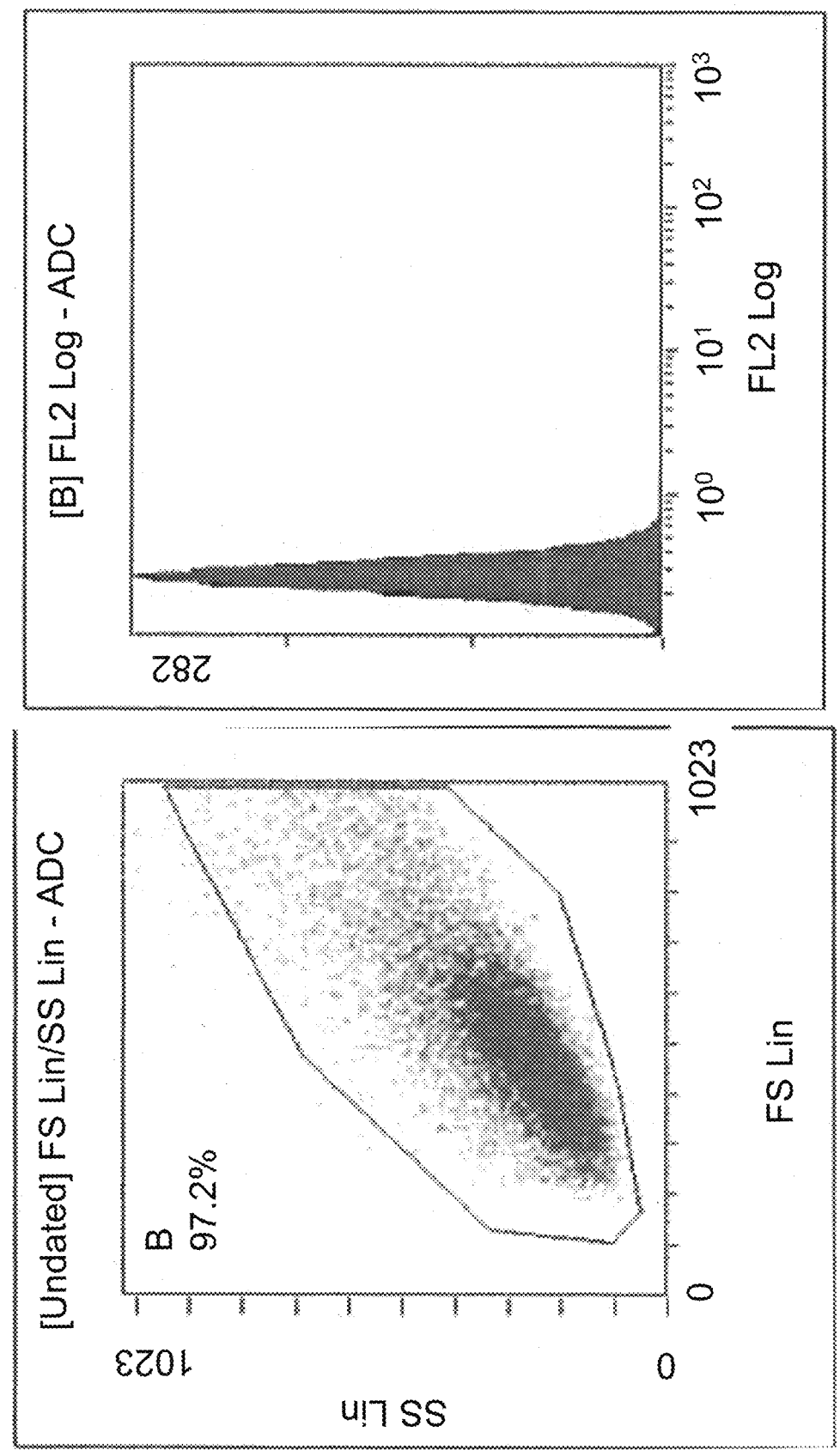
Figure 10B:
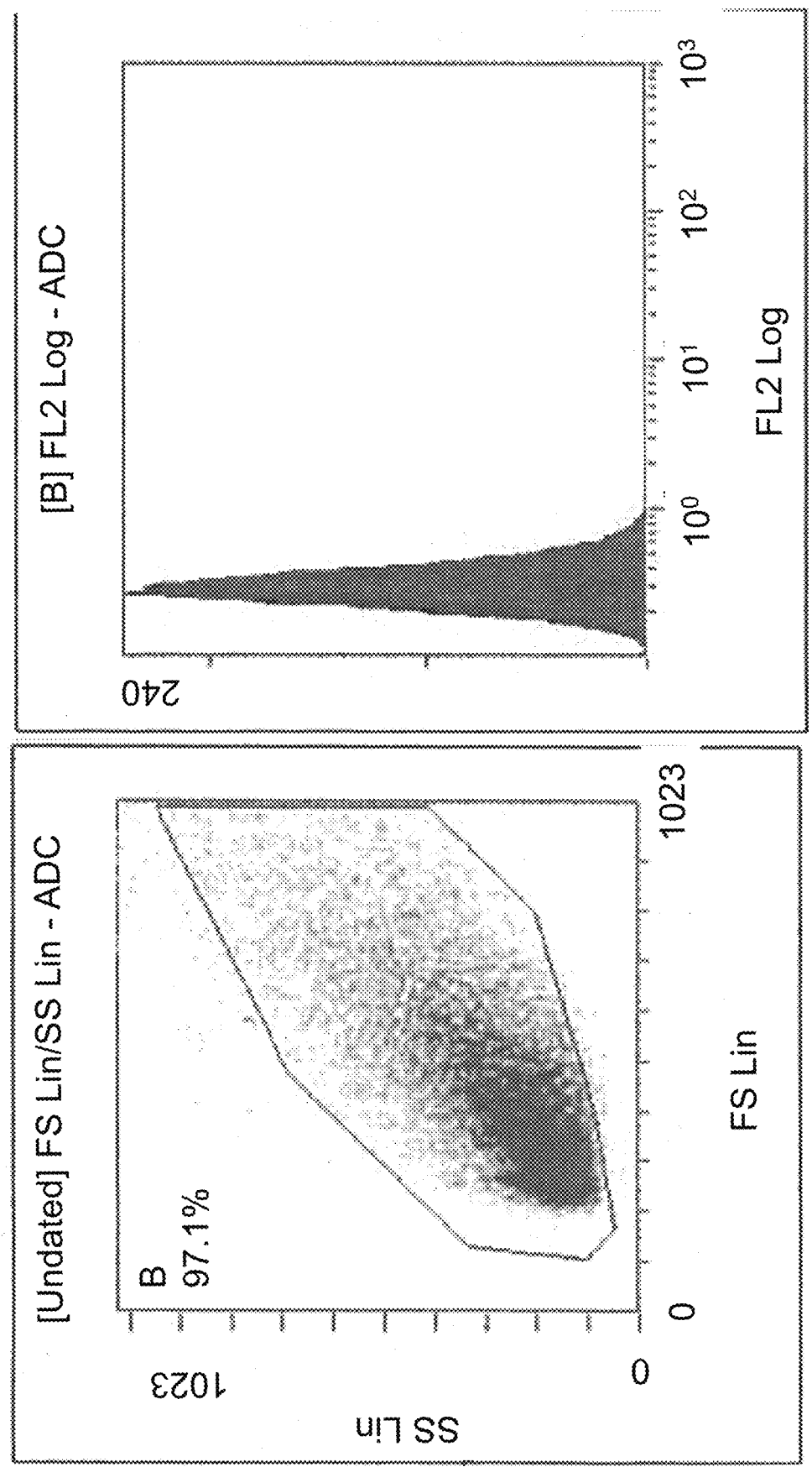

Further, setting of a flow cytometer was performed by the same method as described above with reference to FIGS. 1 to 4B. The display of the flow cytometer was confirmed by using a first plot (two-dimensional plot: X axis=FS(Log), Y axis=SS(Log)) and a sixth plot (histogram of FL2: X axis=FL2(Log), Y axis=the number of events) obtained by measurement in this Example. Herein, a first plot and a sixth plot obtained by measuring the OVCAR-3 cell by flow cytometry are shown in FIGS. 8A and 8B. The FIG. 8A represents measurement results of the sample subjected to lipid staining according to the method of the present disclosure, and the FIG. 8B represents measurement results of the sample not subjected to lipid staining. Similarly, a first plot and a sixth plot obtained by measuring the A431 cell by flow cytometry are shown in FIGS. 9A and 9B (FIG. 9A: the lipid-stained sample, FIG. 9B: lipid-non-stained sample), and a first plot and a sixth plot obtained by measuring the PC3 cell by flow cytometry are shown in FIGS. 10A and 10B (FIG. 10A: the lipid-stained sample, FIG. 10B: lipid-non-stained sample).

From the results shown in FIGS. 8A to 10B, average values of X-axis address were, from the results of the sixth plot of positive control in the measurement of respective cells, 150 in the OVCAR-3 cell (FIGS. 8A and 8B), 24.7 in the A431 cell (FIGS. 9A and 9B), and 12.8 in the PC3 cell (FIGS. 10A and 10B), and the expression amount of the EpCAM (CD326) antigen on the surfaces of respective parent cells was PC3 <(1.9 times)<A431<(11.7 times) <OVCAR-3.

Meanwhile, the lipid bilayer membrane particles (extracellular vesicles) were caused to be expressed from the parent cells prepared above. Specifically, after exchange of a culture medium (RPMI+10% FBS, filtered with a 0.2 μm filter), each cell was subjected to $CO_2$ incubation for 24 hours so that the lipid bilayer membrane particles (extracellular vesicles) were caused to be expressed from each cell. Then, 10 mL of the sample subjected to incubation was subjected to centrifugation at 500×g for 10 minutes to remove de novo cells and large apoptosis fragments before being attached to the dish. Subsequently, the obtained centrifugation supernatant was subjected to centrifugation at 20000×g for 1 hour and the obtained pellet was stored by freezing. Then, the sample was melted before measurement and suspended in FBS filtered with a 0.2 μm filter to obtain a sample for preparation. Subsequently, the sample for preparation was subjected to positive selection by using a magnetic bead labeled with an anti-EpCAM antibody and the selected sample was used as a sample for measurement.

Figure 11A:
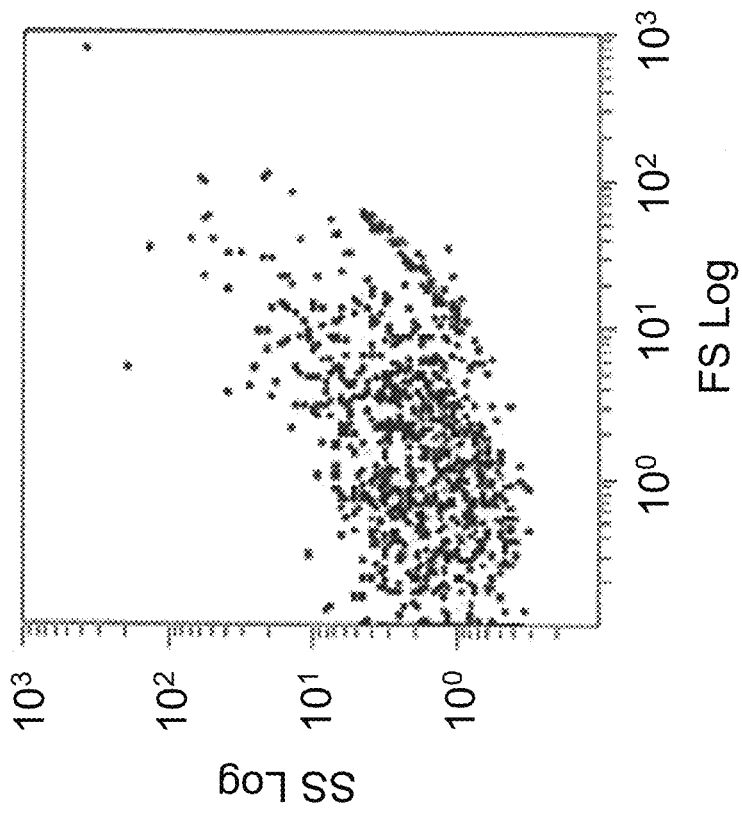
FIGS. 11A and 11B present flow cytometry results obtained by measuring extracellular vesicles (EVs) derived from OVCAR-3 cells which were subjected to lipid staining.
Figure 11B:
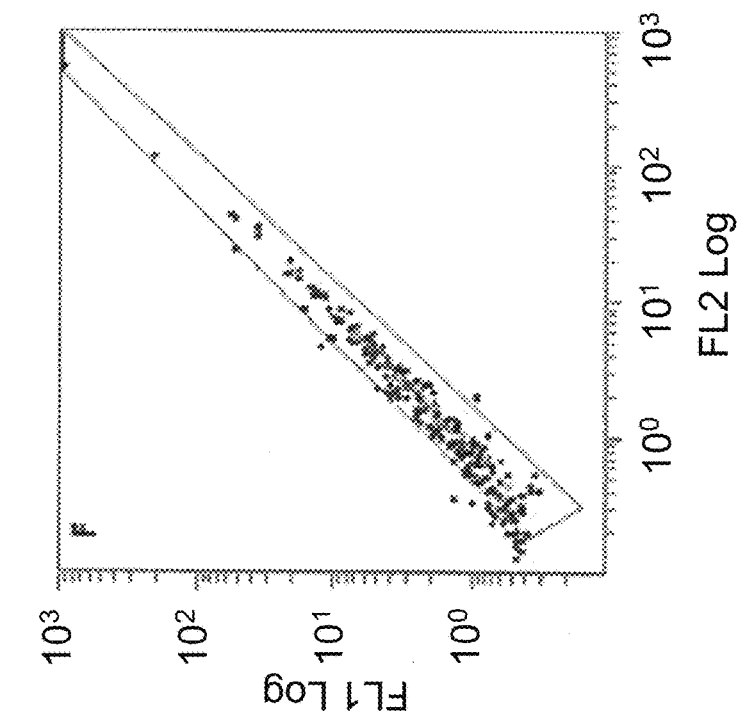
Figure 12A:
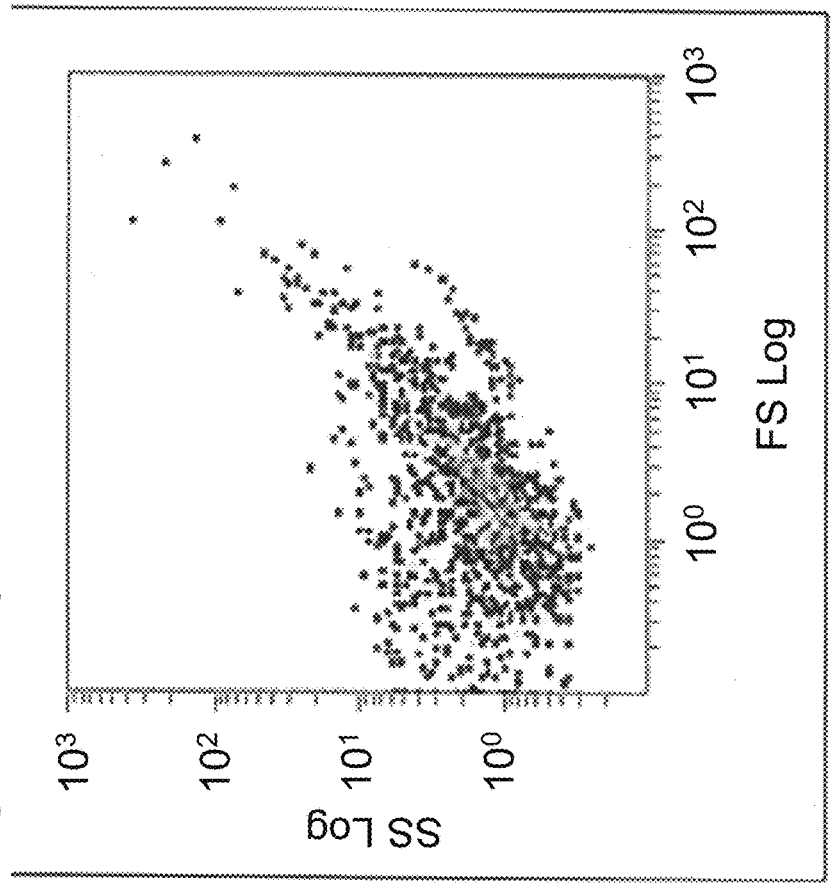
FIGS. 12A and 12B present flow cytometry results obtained by measuring EVs derived from A431 cells which were subjected to lipid staining.
Figure 12B:
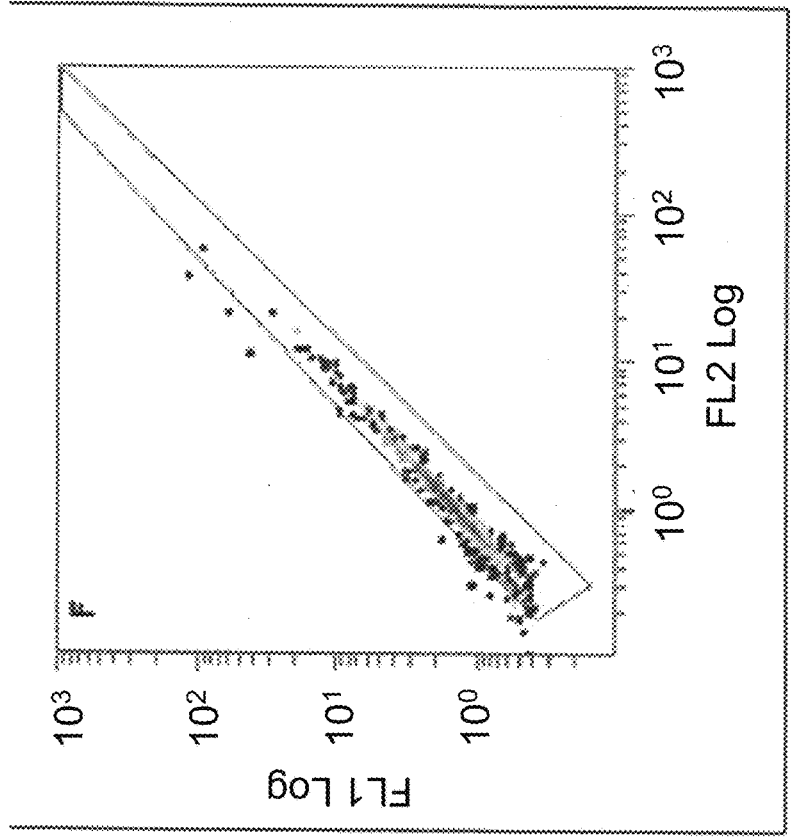
Figure 13A:
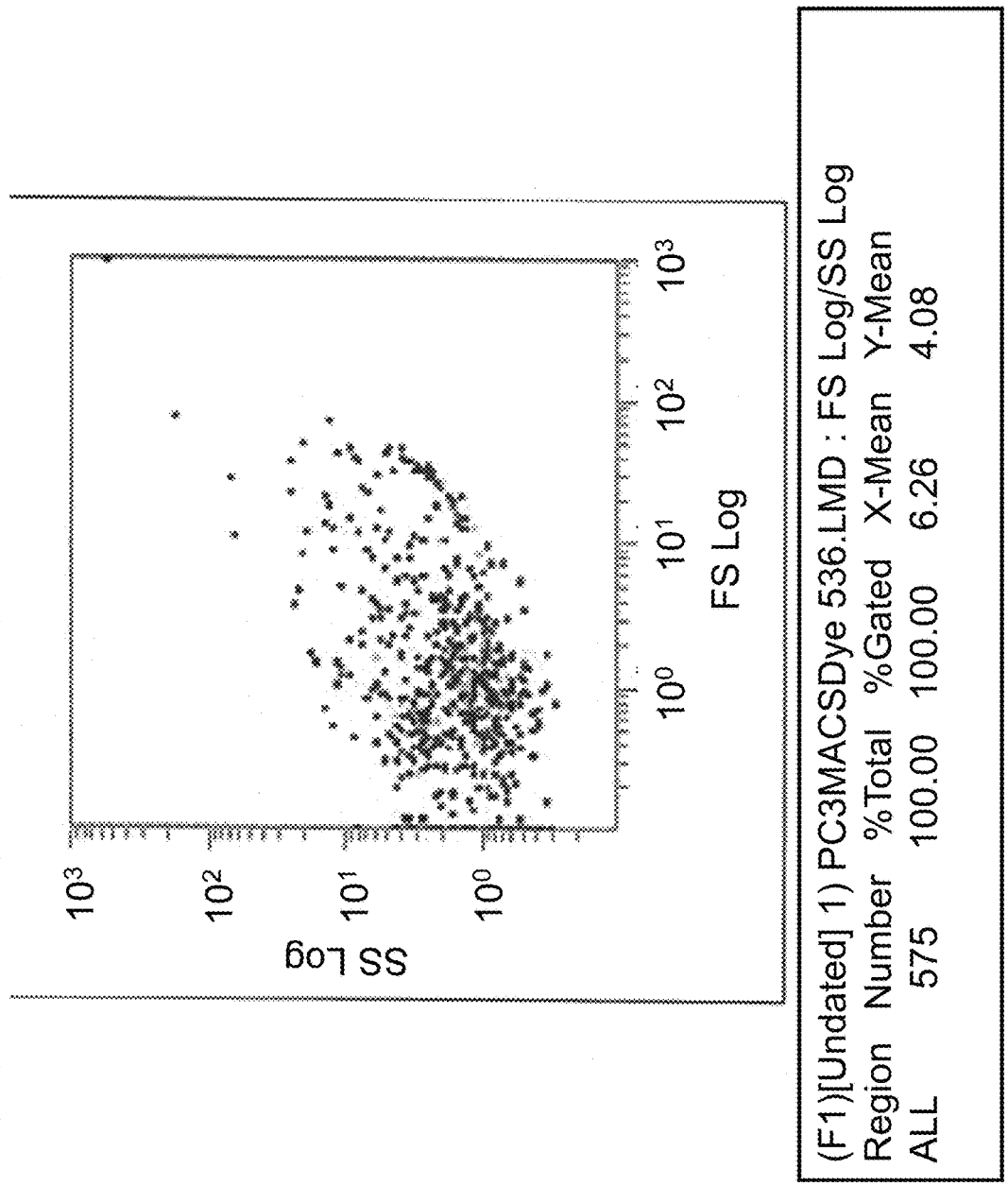
FIGS. 13A and 13B present results obtained by measuring EVs derived from PC3 cells which were subjected to lipid staining.
Figure 13B:
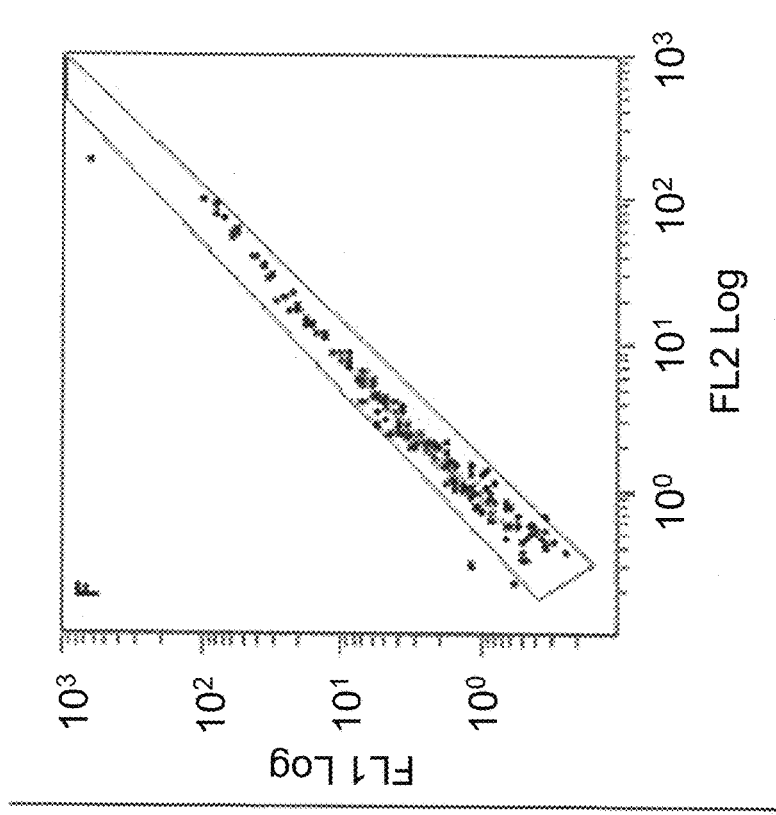

Thereafter, after setting of the flow cytometer was performed again in the same manner as described above, the sample for measurement was measured. The display of the flow cytometer was confirmed by using a first plot (two-dimensional plot: X axis=FS(Log), Y axis=SS(Log)) and a second plot (two-dimensional plot: X axis=FL2(Log), Y axis=FL1(Log)) obtained by measurement in this Example. The plots (the first plot and the second plot) obtained in this way are shown in FIGS. 11A to 13B. Each of FIGS. 11A and 11B is a first plot (FIG. 11A) and a second plot (FIGS. 11B) showing results obtained by measuring EVs derived from OVCAR-3 cells which are subjected to lipid staining. Similarly, each of FIGS. 12A and 12B is a first plot (FIG. 12A) and a second plot (FIG. 12B) showing results obtained by measuring EVs derived from A431 cells which are subjected to lipid staining, and each of FIGS. 13A and 13B is a first plot (FIG. 13A) and a second plot (FIG. 13B) showing results obtained by measuring EVs derived from PC3 cells which are subjected to lipid staining.

Herein, in the conventionally known method, since the amount of the antigen was detected (quantified) by using the fluorescence intensity of the fluorescent dye marker depending on the amount of the target antigen on the cell surface, there were problems in that the existence of the event that was buried in the noise area was unavoidable, and the detection sensitivity was changed due to a difference in the amount of the target antigen on the cell surface. On the other hand, according to the quantitative determination method according to the present disclosure, as clearly understood from the above-described results, it was confirmed that by using lipid staining, the detection could be performed regardless of the difference in the amount of the target antigen on the cell surface. Incidentally, when proportions of the total events shown in the respective first plots shown in FIGS. 11A to 13B and the number of events in the EV gate in the respective second plots were calculated, the proportions were 44% (502/1149) in the OVCAR-3 cell (FIGS. 11A and 11B), 71% (1134/1605) in the A431 cell (FIGS. 12A and 12B), and 37% (214/575) in the PC3 cell (FIGS. 13A and 13B). Incidentally, in some cases, the intracellular vesicles and the like selected by the magnetic bead are mainly occupied in the total number of the cells detected in the first plot, but a trace amount of non-specific reaction substances or the like caused by protein aggregation or the like is contained. Further, since the intensity of the lipid staining is proportional to the size of the lipid bilayer membrane particles, extremely fine particles are not contained in the EV gate and thus cannot be detected. This depends on the detection sensitivity of the fluorescence intensity of the flow cytometer.

What is claimed is:

1. A method for detecting lipid bilayer membrane particles (LBMPs), or fragments thereof, having predetermined molecules existing on surfaces thereof, in a biological sample collected from a subject, the method comprising:
    adding to the biological sample a dye that stains a lipid bilayer membrane to provide a stained lipid bilayer membrane in the biological sample;
    adding a substance that specifically binds to the predetermined molecules, to provide a substance bound to the predetermined membrane molecules of the stained LBMPs or fragments thereof;
    trapping the substance bound to the predetermined membrane molecules of the stained LBMPs or fragments thereof and separating unbound components in the biological sample therefrom; and
    detecting the separated stained lipid bilayer membrane particles or fragments thereof by measurement of the dye emission spectrum;
    wherein said substance is conjugated to a magnetic bead having a preset particle size selected for the LBMPs or binds to the magnetic bead;
    wherein the trapping and separating said substance steps are performed magnetically; and
    wherein the particle size of the magnetic bead is further configured to equal to or less than the minimum detection sensitivity of the measurement system.

2. The method according to claim 1, wherein the substance binds to the magnetic bead.

3. The method according to claim 2, wherein the substance can directly bind to the magnetic bead by functional group modification of the magnetic bead.

4. The method according to claim 1, wherein the substance is labeled with biotin, and the magnetic bead is labeled with avidin or an anti-biotin antibody which can bind to biotin.

5. The method according to claim 1, wherein the magnetic bead is subjected to a blocking treatment.

6. The method according to claim 1, wherein the substance is an antibody or an engineered antibody.

7. The method according to claim 1, wherein the substance is not labeled with a fluorescent dye.

8. The method according to claim 1, wherein the predetermined molecule is a membrane protein.

9. The method according to claim 8, wherein the membrane protein is one or more of CD antigens selected from the group consisting of CD63, CD81, CD9, CD82, CD151, CD326, CD144, CD105, CD146, CD62E, CD142, CD41a, CD62P, CD61, CD11b, CD32, CD33, CD14, CD66b, CD56, CD16, and CD64.

10. The method according to claim 9, wherein the membrane protein is CD 63, CD81 or both.

11. The method according to claim 9, wherein the membrane protein is at least one CD antigen selected from the group consisting of CD63, CD81, and CD9.

12. The method according to claim 9, wherein the membrane protein is at least one CD antigen selected from the group consisting of CD326, CD142, and CD144.

13. The method according to claim 1, wherein the step of detecting the separated lipid bilayer membrane particles or fragments thereof is performed by using flow cytometry or imaging cytometry.

14. The method according to claim 13, wherein the intensities of fluorescence emissions of two or more different fluorescence wavelengths are measured simultaneously in the detecting step.

15. The method according to claim 13, wherein the number of LBMPs or fragments thereof is measured in the detecting step.

16. The method according to claim 13, wherein the size of LBMPs or fragments thereof is measured by using scattered light intensity data or lipid staining fluorescence intensity data in the detecting step.

17. The method according to claim 1, wherein detecting the separated lipid bilayer membrane particles or fragments thereof is performed by flow cytometry or imaging cytometry, and wherein the intensities of the fluorescence emissions of two or more different fluorescence wavelengths are measured simultaneously.

18. A detection kit for lipid bilayer membrane particles or fragments thereof, the detection kit comprising:
    a dye that stains a lipid bilayer membrane in a biological sample;

a substance that specifically binds to predetermined molecules existing on surfaces of the lipid bilayer membrane particles or fragments thereof; and a separating reagent comprising magnetic beads having a preset particle size selected for the LBMPs for trapping the substance and separating the lipid bilayer membrane particles or fragments thereof wherein the particle size of the magnetic based is further configured to be equal to or less than the minimum detection sensitivity of the measurement system.

19. The detection kit according to claim 18, further comprising a detector for detecting the separated lipid bilayer membrane particles or fragments thereof on the basis of emission of the dye emission spectrum.

* * * * *